(12) United States Patent
Isaacson et al.

(10) Patent No.: US 7,124,932 B2
(45) Date of Patent: Oct. 24, 2006

(54) ELECTROSURGICAL COUNTER AND LOCKOUT MECHANISM

(75) Inventors: James D. Isaacson, Salt Lake City, UT (US); Paul R. Borgmeier, Salt Lake City, UT (US); William Miller, Bluffdale, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 0 days.

(21) Appl. No.: 10/873,380

(22) Filed: Jun. 21, 2004

(65) Prior Publication Data

US 2005/0183656 A1    Aug. 25, 2005

Related U.S. Application Data

(60) Provisional application No. 60/547,675, filed on Feb. 25, 2004.

(51) Int. Cl.
*G06M 1/28* (2006.01)

(52) U.S. Cl. .................. 235/144 SM; 235/14 SP

(58) Field of Classification Search .................. 235/79, 235/117 R, 117 A, 144 SM, 144 SP, 91 ALL, 235/78 R
See application file for complete search history.

(56) References Cited

U.S. PATENT DOCUMENTS

2002/0091327 A1* 7/2002 Rosenheimer .............. 600/486

* cited by examiner

*Primary Examiner*—Karl D. Frech
(74) *Attorney, Agent, or Firm*—Workman Nydegger

(57) ABSTRACT

An electrosurgical apparatus having a counter/lockout mechanism that monitors the number of sterilization/use cycles the electrosurgical apparatus undergoes and indicates the number of sterilization/use cycles that have actually been performed. The counter/lockout mechanism includes a temperature actuated element actuated in response to each sterilization cycle and a mechanically actuated element in response to a use cycle to effectuate a change of one or a plurality of indicia. The counter/lockout mechanism causes a single increment or decrement for each sterilization/use cycle that has been completed while also impeding use of the electrosurgical apparatus when the electrosurgical apparatus has undergone a predetermined number of sterilization/use cycles. In one embodiment, the distance of movement of the mechanically actuated element when fully actuated is greater than the distance the indicator moves when illustrating a change in the number of remaining uses.

33 Claims, 17 Drawing Sheets

ELECTROSURGICAL COUNTER AND LOCKOUT MECHANISM

CROSS-REFERENCE TO RELATED APPLICATIONS

This application claims benefits from U.S. Provisional Patent Application No. 60/547,675, filed on Feb. 25, 2004, and entitled "Electrosurgical Counter and Lock-Out Mechanism," the contents of which are incorporated herein by reference.

BACKGROUND OF THE INVENTION

1. The Field of the Invention

The present invention relates to electrosurgical apparatuses. In particular, the present invention relates to a counter and lockout device for use with an electrosurgical apparatus to indicate to the user the number of sterilization/use cycles the electrosurgical apparatus has undergone and impede use of the electrosurgical apparatus once a predetermined number of sterilization/use cycles have been conducted.

2. The Relevant Technology

Electrosurgical technology is an important tool in modern surgery due to the multi-functional abilities of electrosurgical instruments and apparatuses. Many electrosurgical instruments and apparatuses are reusable. Reusable electrosurgical instruments undergo sterilization following electrosurgery to ensure that the instruments are clean and sterile for subsequent surgeries. Sterilization procedures can be costly to perform and also result in wear on the reusable instruments and apparatuses. Heat is utilized in many sterilization procedures to kill the micro-organisms, bacteria, and other potential sources of infection that may be present on electrosurgical instruments subsequent to use. As with other forms of sterilization, the heat used in these procedures can be wearing on reusable electrosurgical instruments and apparatuses. As a result, reusable instruments and apparatuses must be designed to withstand the necessary sterilization procedures.

While disposable electrosurgical instruments and apparatuses may not be specifically designed to withstand numerous sterilization and use cycles, such instruments may nevertheless withstand a limited number of use and sterilization cycles before needing to be discarded. Due to this fact, some electrosurgical instruments have been accepted as reusable for a predetermined number of sterilization/use cycles. One difficulty related to these limited reuse instruments is that it can be difficult to monitor the number of sterilization/use cycles a particular tool or apparatus has undergone. As a result, an instrument or apparatus may be disposed of before the predetermined number of uses have been completed. It is also possible that, due to an oversight of a practitioner, an electrosurgical instrument or apparatus may be utilized for more than the recommended number of uses.

A variety of mechanisms and systems for monitoring the number of sterilization/use cycles an electrosurgical instrument or apparatus has undergone have been developed in an attempt to prevent under or over use of a limited reuse electrosurgical instrument or apparatus. One illustrative system for monitoring the number of sterilization/use cycles utilizes a temperature responsive member to increment or decrement a counter in response to a sterilization cycle. However, the manner in which sterilization cycles are conducted has rendered such temperature responsive mechanisms inaccurate or completely ineffective. This is due to the fact that sterilization procedures employ heating and cooling cycles in which multiple temperature peaks and valleys are experienced by the electrosurgical instrument during a single sterilization procedure. This can lead to multiple actuations of the temperature responsive element during a single sterilization procedure. As a result, the counter may increment/decrement multiple times in a single sterilization cycle resulting in an inaccurate representation of the number of sterilization/use cycles that the electrosurgical apparatus has actually undergone. An additional complicating factor is that a variety of types and configurations of sterilization procedures utilize widely variable cycle lengths making it difficult to design a sterilization responsive mechanism that is actuated a single time for each sterilization procedure.

BRIEF SUMMARY OF THE INVENTION

The present invention relates to an electrosurgical apparatus having a counter/lockout mechanism for use with an electrosurgical apparatus. The counter/lockout mechanism monitors the number of sterilization/use cycles the electrosurgical apparatus has undergone and indicates the number of sterilization/use cycles that have actually been performed.

The counter/lockout mechanism can include an indicator for showing the number of sterilization/use cycles the electrosurgical apparatus has undergone. In one embodiment of the present invention, the indicator is decremented or incremented during each sterilization/use cycle, utilizing a temperature actuated element and a mechanically actuated element. The temperature actuated element is actuated in response to each sterilization procedure. The mechanically actuated element is actuated in response to each use of the instrument. By utilizing the combination of a temperature actuated element and a mechanically actuated element to effectuate a change of the counter, the counter/lockout mechanism results in a single decrement or increment of the indicator for each completed sterilization/use cycle.

The counter/lockout mechanism can also be adapted to prevent use of the electrosurgical apparatus after the electrosurgical apparatus has undergone a predetermined number of sterilization/use cycles. In one embodiment of the present invention, the counter/lockout mechanism includes a mechanical plunger that prevents use of the apparatus once a predetermined number of sterilization/use cycles have been conducted.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1A:
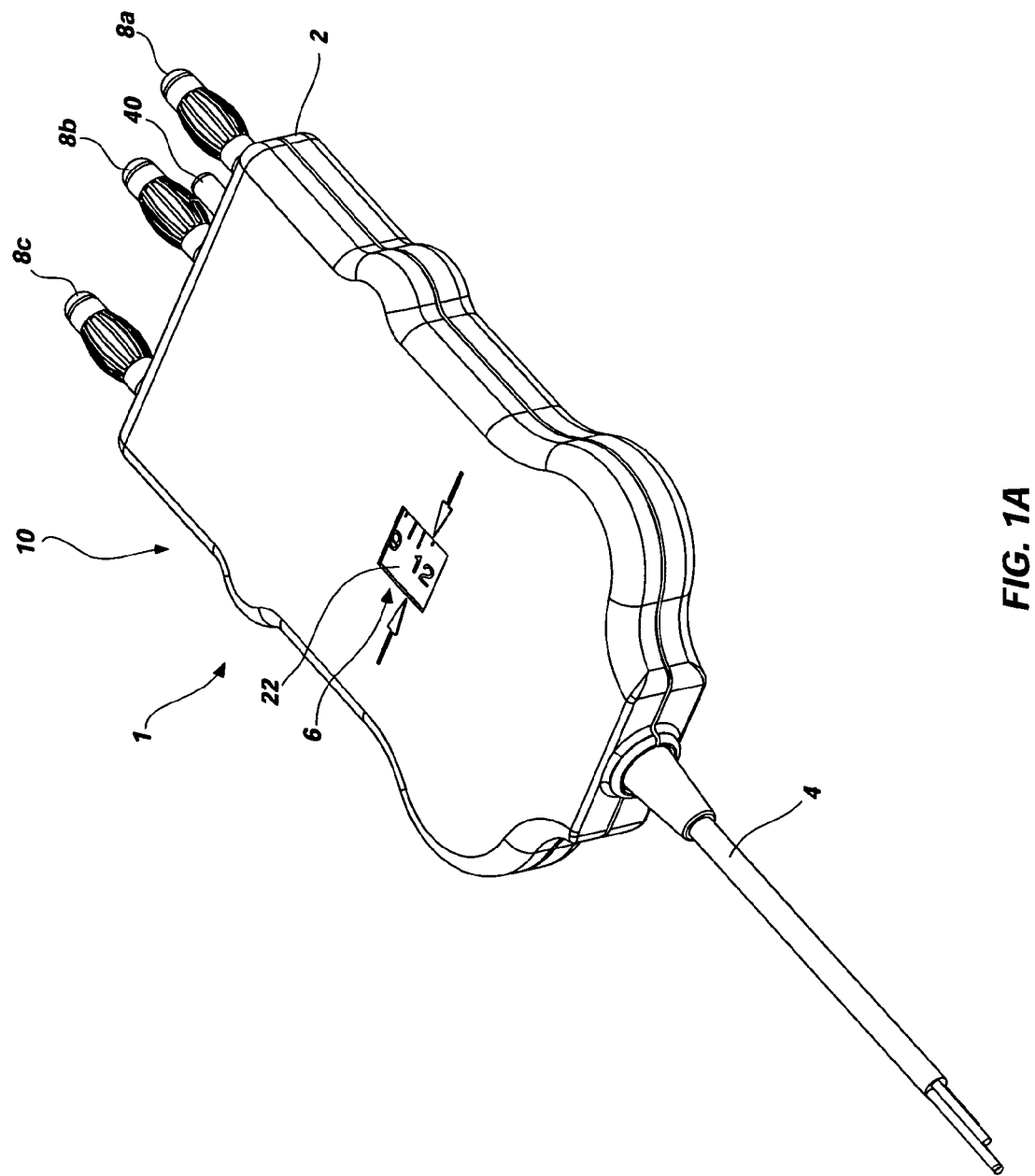
FIG. 1A is a perspective view of a portion of an exemplary counter/lockout mechanism according to one embodiment of the present invention, in which a mechanical plunger is shown in a partially extended position.

The present invention relates to an electrosurgical apparatus having a counter/lockout mechanism. The electrosurgical counter/lockout mechanism of the present invention is designed to perform two primary functions. First, it performs a counter function so as to track the number of sterilization/use cycles the electrosurgical apparatus has undergone and displays to the user the number of sterilization/use cycles undergone and/or the number of sterilization/use cycles remaining. Second, once the electrosurgical apparatus has undergone a predetermined number of sterilization/use cycles, the counter/lockout mechanism performs a lockout function so as to prevent the use of the electrosurgical apparatus in any further electrosurgical procedures.

According to one aspect of the present invention, the counter/lockout mechanism includes an indicator for displaying the number of sterilization/use cycles remaining before the electrosurgical apparatus should be discarded. The indicator is incremented/decremented utilizing a temperature actuated element and a mechanically actuated element (e.g. mechanical plunger). The temperature actuated element is actuated in response to each sterilization cycle undergone, while the mechanically actuated element is actuated in response to each use cycle conducted. By utilizing the combination of a temperature actuated element and a mechanically actuated element, multiple increments/decrements of the counter are eliminated during a single sterilization/use cycle.

According to one aspect of the present invention, an actuator is utilized in connection with the temperature actuated element and the mechanically actuated element to increment/decrement the indicator. In the embodiment, the temperature actuated element moves the actuator in a first direction during a sterilization cycle. When the actuator is moved in the first direction the indicator is not incremented or decremented. As a result, multiple temperature spikes that may occur during a single sterilization procedure will not result in multiple counter changes. In contrast, the mechanically actuated element moves the actuator in a second direction during a use cycle resulting in incrementing/decrementing of the indicator. A portion of the mechanically actuated element (e.g., a mechanical plunger) extends from the electrosurgical apparatus. When the electrosurgical apparatus is used by the practitioner, such as by inserting a plug portion of the apparatus into electrical engagement with an electrosurgical generator, the mechanically actuated element is depressed. Depression of the mechanically actuated element moves the actuator in the second direction and results in an increment/decrement of the indicator. The actuator is prevented from causing another increment/decrement of the indicator until the temperature actuated element again moves the actuator in the first direction during a subsequent sterilization cycle. By utilizing the combination of a temperature actuated element and a mechanically actuated element to effectuate a change of the indicator, the counter/lockout mechanism results in a single increment/decrement for each sterilization/use cycle that has been completed.

According to another aspect of the present invention, the counter/lockout mechanism impedes use of the electrosurgical apparatus when the electrosurgical apparatus has undergone a predetermined number of sterilization/use cycles. In one embodiment of the present invention, the counter/lockout mechanism includes a mechanical plunger that physically impedes use of the apparatus once the predetermined number of sterilization/use cycles has been conducted.

Figure 8:
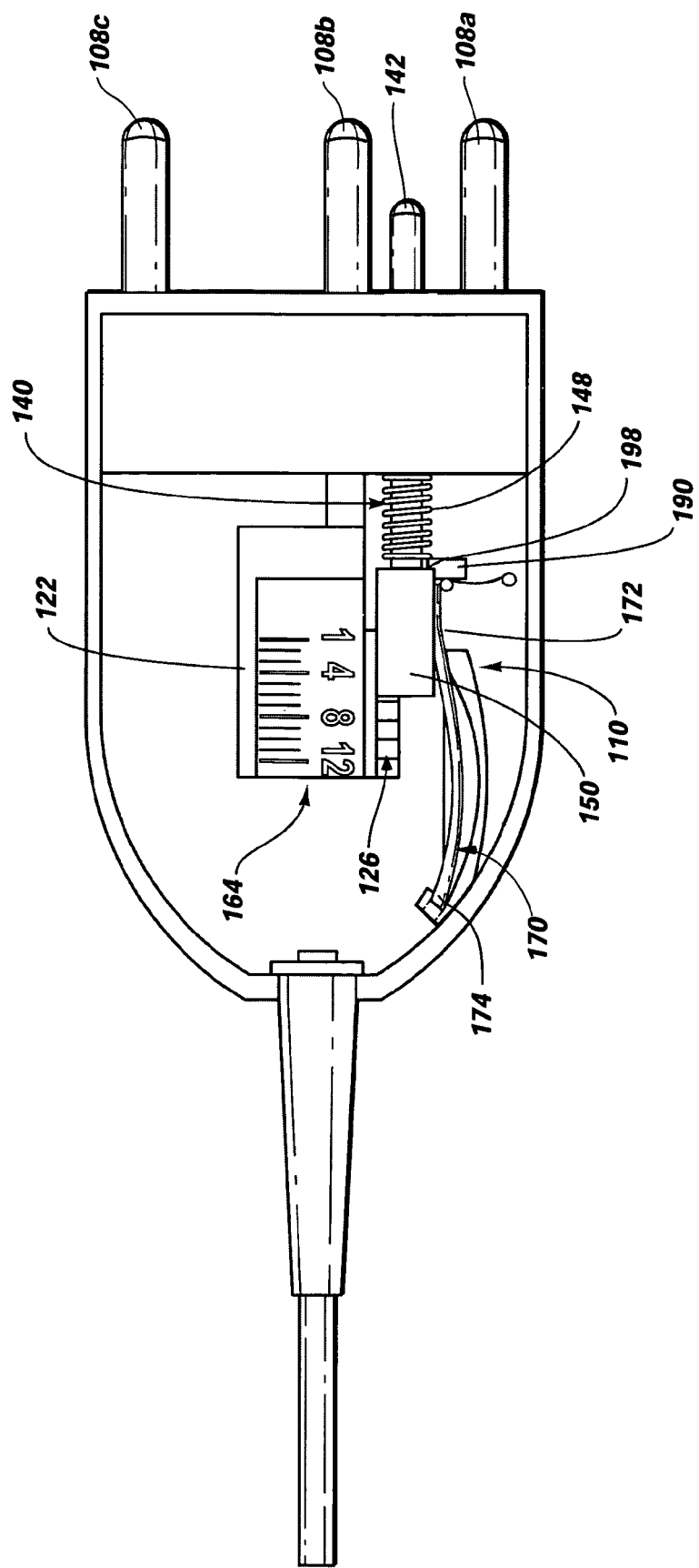
FIG. 8 is a top internal view of the embodiment shown in FIG. 5, illustrating the internal workings of the counter/lockout mechanism during a sterilization procedure.
Figure 9:
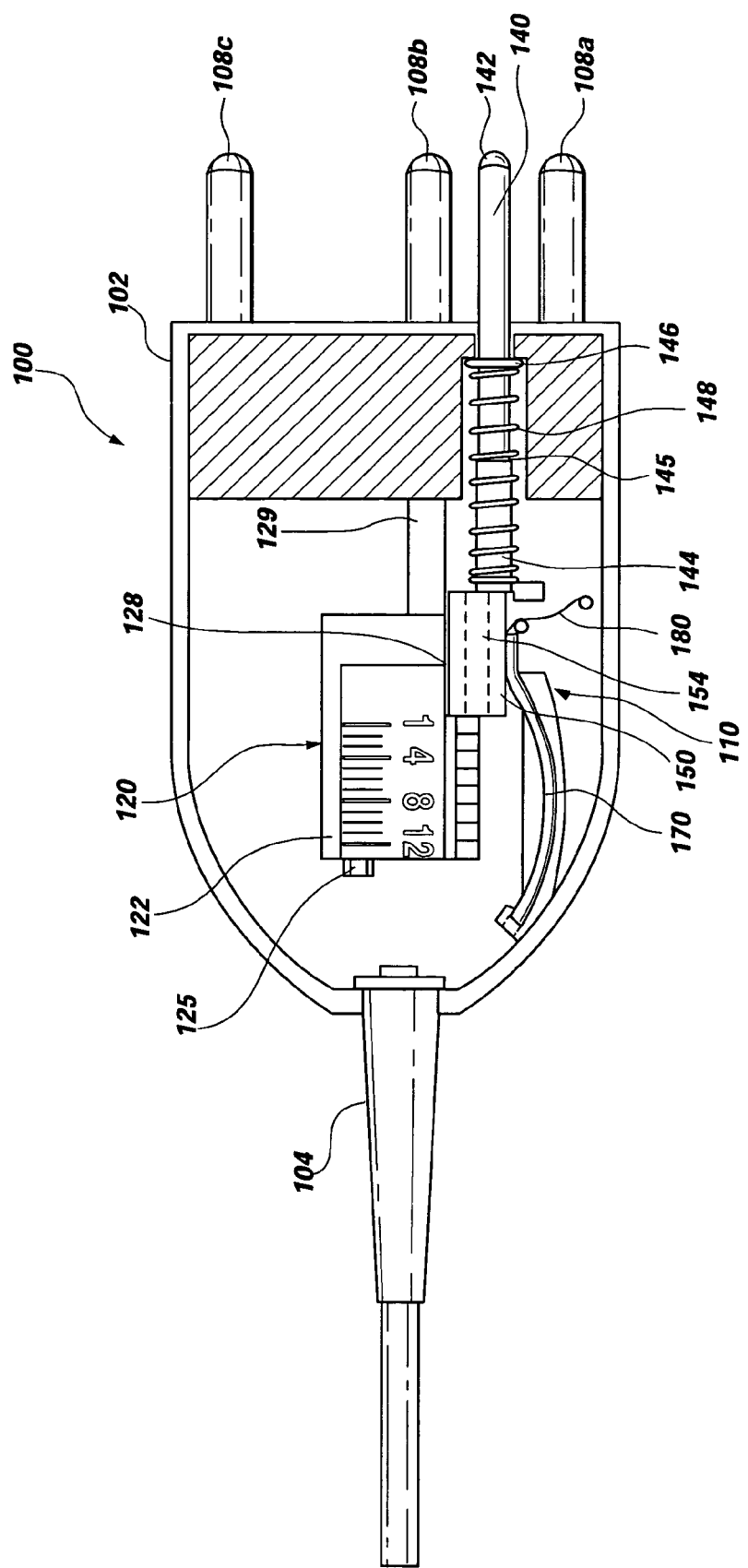
FIG. 9 is a partial cross-sectional view of the embodiment shown in FIG. 5, illustrating the mechanical plunger of the counter/lockout mechanism in a fully extended, lockout position.
Figure 10:
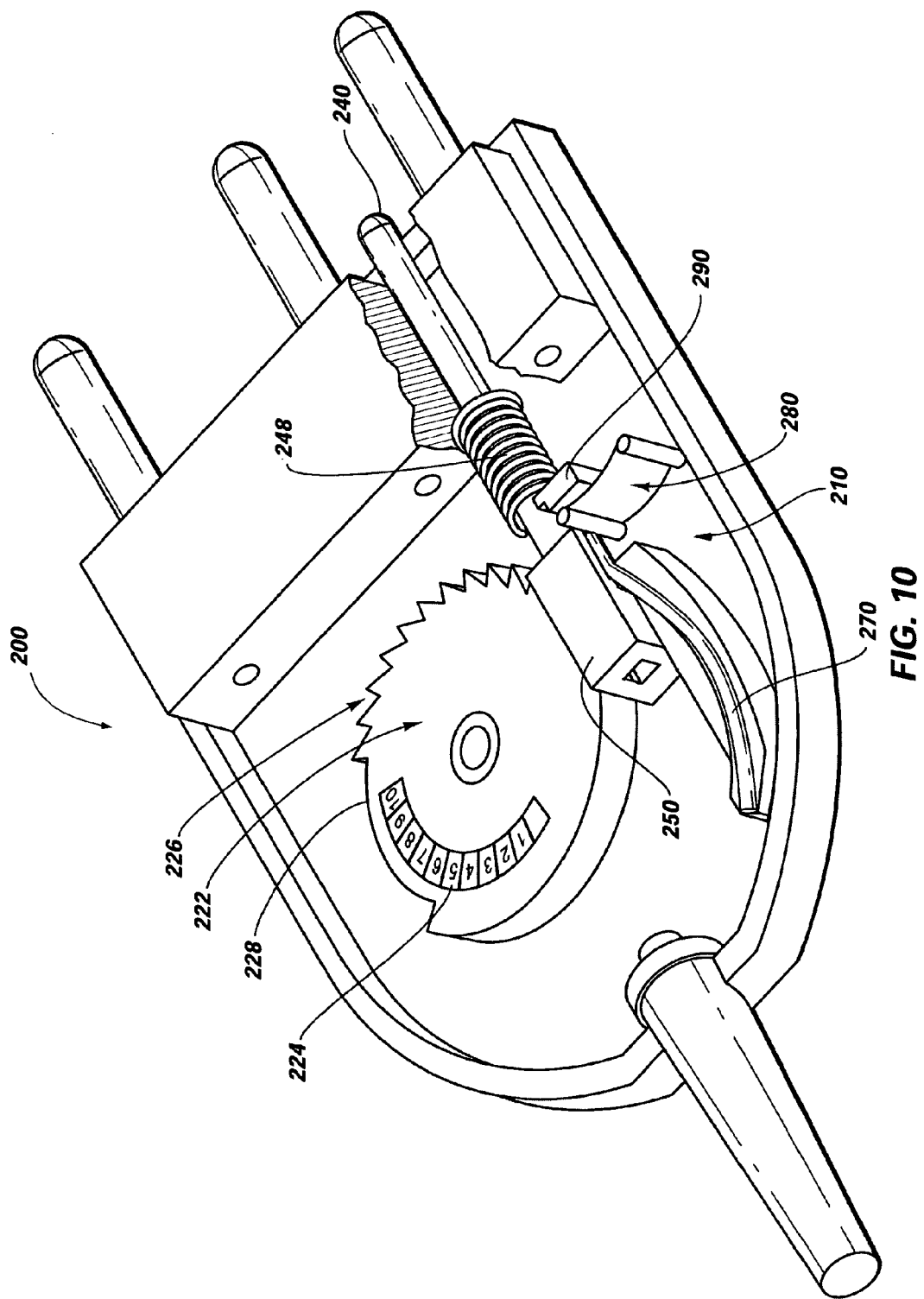
FIG. 10 is an internal perspective view of yet another exemplary embodiment of the counter/lockout mechanism according to the present invention.

Referring now to the drawings, FIGS. 1 through 4B illustrate a first embodiment in accordance with the present invention, FIGS. 5 through 9 illustrate a second embodiment in accordance with the present invention, and FIG. 10 illustrates a third embodiment in accordance with the present invention.

As used herein, the following terms shall have the following meanings:

The term "sterilization/use cycle" shall refer to the sterilization and use of an electrosurgical apparatus, regardless of the order in which such activities are considered to occur. While the present invention is described in the context of a "sterilization/use cycle," it should be understood that the teachings of the present invention are broad enough, and are intended to include, the situation in which the "use" proceeds the "sterilization" and vice versa; the point being that between each consecutive use of the electrosurgical apparatus (whether the sterilization procedure is considered to occur before or after a given use), the counter/lockout mechanism of the present invention only decrements/increments by a single indicia.

The term "decrement/increment" shall refer to the decrease or increase of the indicia of use incorporated in the counter/lockout mechanism of the present invention to indicate completion of a sterilization/use cycle. While the embodiments of the present invention disclosed herein are described the context of "decrementing" the counter/lockout mechanism for each sterilization/use cycle, it should be understood that the teachings of the present invention are broad enough, and are intended to include, the case in which the counter/lockout mechanism is "incremented" for each sterilization/use cycle.

In addition, the following conventions will be used herein in describing the orientation of various components of the counter/lockout mechanism of the present invention:

With reference to electrosurgical instruments in general, the "distal end" typically refers to the active electrode through which electrosurgery is performed on a patient. Inasmuch as the preferred embodiments of the counter/lockout mechanism of the present invention disclosed herein are housed within a plug used to connect an electrosurgical electrode to an electrosurgical generator, the "distal end" shall refer to that end of the counter/lockout mechanism located closest to the electrosurgical instrument (i.e., the end closest to wire 4 in FIG. 1A) and the "proximal end" shall refer to that end of the counter/lockout mechanism located farthest away from the electrosurgical instrument (i.e., the end with prongs 8a–c in FIG. 1A). The orientation of various components making up the counter/lockout mechanism of the present invention may also be sometimes expressed in similar terms.

Referring now to the embodiment shown in FIGS. 1 through 4B, which illustrate a first embodiment in accordance with the present invention, an electrosurgical apparatus 1 includes a counter/lockout mechanism 10. The counter/lockout mechanism 10 is positioned in a power source connector of the electrosurgical apparatus 1 that is configured to be plugged into a source of electrosurgical power, such as an electrosurgical generator (not shown). Electrosurgical apparatus 1 includes a housing 2 for protecting the internal components of electrosurgical apparatus 1, a power cord 4 for the delivery of electrosurgical current from the generator (not shown) to an electrosurgical instrument (not shown), a window 6 for viewing one or a plurality of indicia on an indicator 22, and prongs 8a–c for connecting electrosurgical apparatus 1 to an electrosurgical power source (not shown).

Turning to a discussion of FIG. 1A, the counter/lockout mechanism is included as part of electrosurgical apparatus 1. The counter/lockout mechanism tracks the number of sterilization/use cycles electrosurgical apparatus 1 has undergone and impedes the use of the electrosurgical apparatus 1 once a predetermined number of sterilization/use cycles have been completed. Discussion will be made herein of how the components of the counter/lockout mechanism function together to track the number of sterilization/use cycles conducted and subsequently impede further use of the apparatus. As will be appreciated by those skilled in the art, a variety of types and configurations of mechanisms can be utilized without departing from the scope and spirit of the present invention. For example, in one embodiment a counter mechanism may be utilized without a lockout mechanism. In another embodiment, a lockout mechanism may be utilized without a counter mechanism.

In the illustrated embodiment, the counter/lockout mechanism includes an indicator 22 and a mechanical plunger 40. Indicator 22 includes a plurality of indicia which show the number of sterilization/use cycles that have been completed, or that are remaining, to allow a user to ascertain when the electrosurgical apparatus should be discarded. During each sterilization/use cycle indicator 22 is incremented/decremented to indicate the change in the number of sterilization/use cycles that have been completed. In this manner, the electrosurgical apparatus 1 tracks the number of remaining sterilization/use cycles electrosurgical apparatus 1 can undergo without requiring that the user separately track the number of sterilization/use cycles.

For illustrative purposes, the remaining figures will be discussed in reference to a counter/lockout mechanism which displays the number of remaining uses before the electrosurgical apparatus should be discarded and utilizes an indicator that is decremented subsequent to each sterilization/use cycle. As will be understood by those skilled in the art, a variety of types and configurations of methods and mechanisms for displaying when the electrosurgical apparatus should be discarded can be utilized without departing from the scope and spirit of the present invention. For example, in one embodiment the counter/lockout mechanism may indicate the number of sterilization/use cycles that have been conducted and utilizes an indicator that is incremented subsequent to each sterilization/use cycle. In another embodiment, the number of sterilization/use cycles may be displayed as the number of completed sterilization/use cycles relative to the total number of sterilization/use cycles that can be conducted (i.e. 1 of 4, 2 of 4, etc.) In another embodiment, the counter/lockout mechanism may not display the number of sterilization/use cycles conducted but rather may internally monitor the number of sterilization/use cycles. In the embodiments illustrated and described herein, the lockout position of the mechanical plunger is used to indicate to the user that the electrosurgical apparatus should be discarded. In another embodiment, a mechanism other than an indicator may be used to indicate to the user when the electrosurgical apparatus should be discarded.

As will be appreciated by those skilled in the art, a variety of types and configurations of indicators can be utilized without departing from the scope and spirit of the present invention. For example, in one embodiment the indicator is decremented subsequent to a sterilization cycle but will not be decremented a subsequent time until a subsequent use cycle and a sterilization cycle are conducted. In another embodiment, the indicator indicates the number of remaining sterilization/use cycles that can be performed before the electrosurgical apparatus should be discarded. In yet another embodiment, the indicator indicates the total number of sterilization/use cycles that have been conducted.

Mechanical plunger 40 operates in connection with other components of electrosurgical apparatus 1 to allow for proper functioning of the counter/lockout mechanism 10 utilized with electrosurgical apparatus 1. For example, mechanical plunger 40 operates in connection with other components of counter/lockout mechanism 10 to decrement the indicia on indicator 22. In the illustrated embodiment, mechanical plunger 40, is positioned between prongs 8a and 8b such that mechanical plunger 40 will be depressed when prongs 8a–c are inserted into an electrosurgical power source (not shown). When prongs 8a–c are inserted into an electrosurgical power source, mechanical plunger 40 contacts a wall, outlet, or another surface, such as the source's housing, in which prongs 8a–c are inserted, urging mechanical plunger 40 into housing 2.

In the illustrated embodiment, mechanical plunger 40 is in a partially extended position. The partially extended position of mechanical plunger 40 results when the predetermined number of sterilization/use cycles have not been completed. Mechanical plunger 40 is one example of a means for detecting a use cycle. Other such means for detecting a use cycle are known to those skilled in the art. For instance, a software with a chip, electrical lights, bar graphs, and a removable plunger that acts as a key for subsequent uses can be utilized as a means for detecting a use cycle.

As will be appreciated by those skilled in the art, a variety of types and configurations of electrosurgical counter/lockout mechanisms can be utilized with a variety of types and configurations of electrosurgical apparatuses without departing from the scope and spirit of the present invention. For example in one embodiment, the counter/lockout mechanism is utilized in the body of an electrosurgical pen or other instrument rather than in the power source connector. In another embodiment, a counter/lockout mechanism is utilized in a portion of a modularized electrosurgical apparatus that is sterilized after being separated from other portions of the electrosurgical apparatus. In another embodiment, the indicator shows the number of sterilization/use cycles completed as a function of a recommended number of sterilization/use cycles.

Figure 1B:
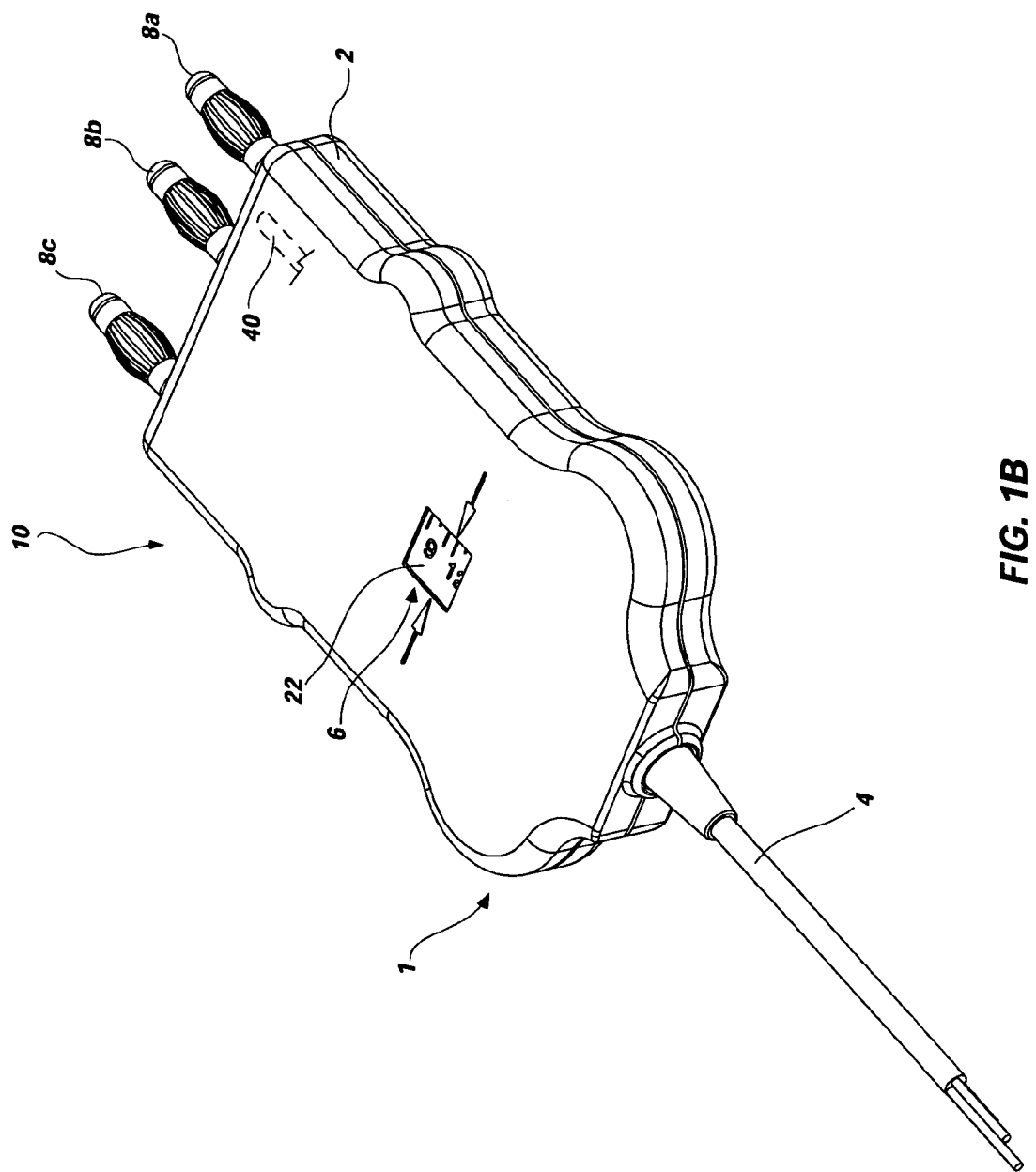
FIG. 1B is a perspective view of the embodiment shown in FIG. 1A, in which the mechanical plunger is shown in a depressed position.

FIG. 1B is a top view of electrosurgical apparatus 1 illustrating mechanical plunger 40 in a depressed position. For the sake of simplicity, prongs 8a–c are not shown as being inserted into an electrosurgical power source. As will be appreciated by those skilled in the art, in a typical use setting mechanical plunger 40 is pushed into housing 2 of electrosurgical apparatus 1 because prongs 8a–c have been inserted into an outlet or other source of electrosurgical current (not shown). As mechanical plunger 40 is pushed into housing 2 of electrosurgical apparatus 1, indicator 22 slides in the direction of power cord 4 effectuating a change of the one or plurality of indicia on indicator 22. The change of the indicia indicates to the user that the number of remaining uses has been decreased by one use from that indicated in FIG. 1A.

Figure 1C:
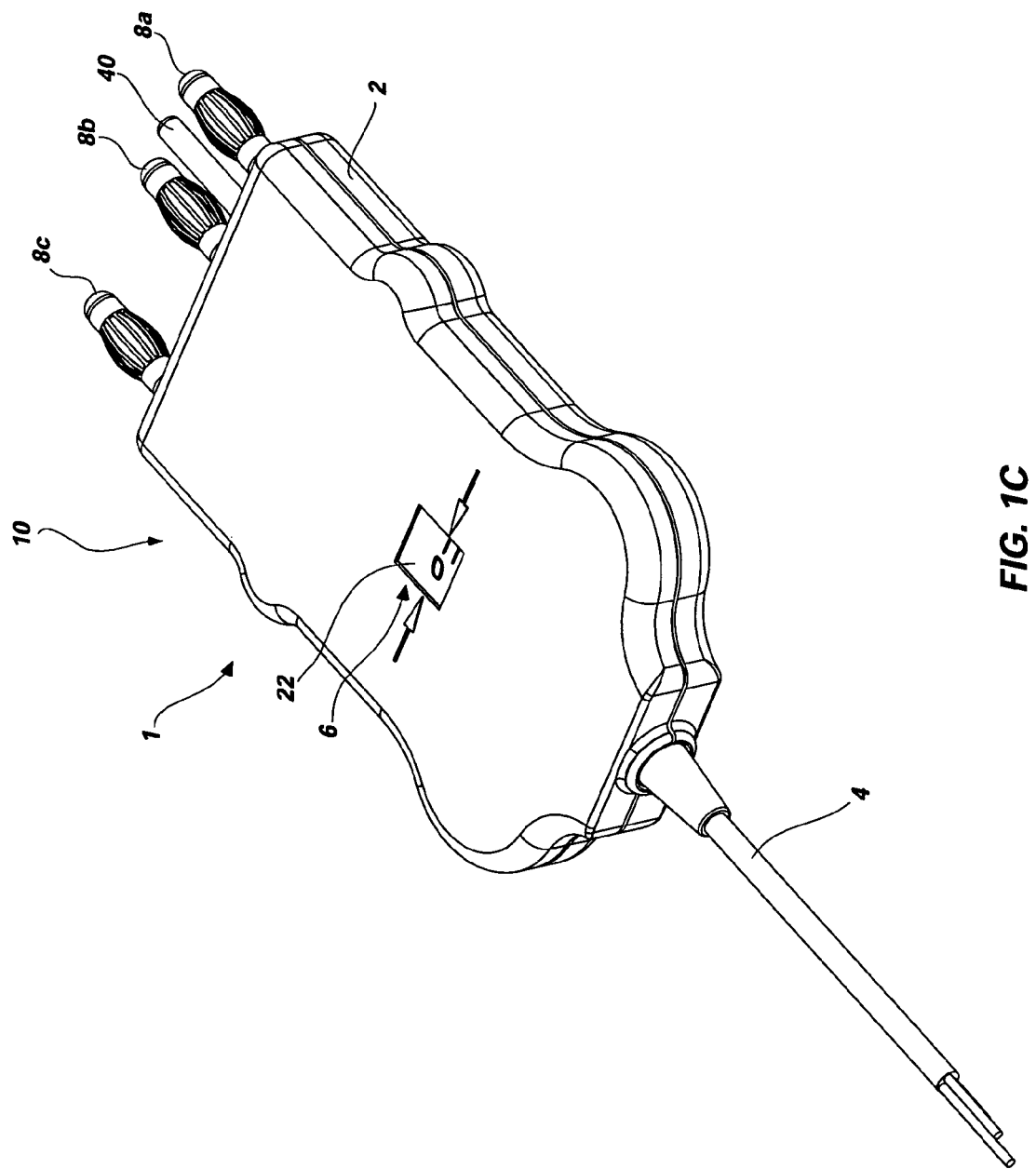
FIG. 1C is a perspective view of the embodiment shown in FIG. 1A, in which the mechanical plunger is illustrated in a fully extended, lockout position.

FIG. 1C illustrates electrosurgical apparatus 1 in which mechanical plunger 40 is in a fully extended position. In the illustrated embodiment, mechanical plunger 40 is extended from housing 2 of electrosurgical apparatus 1 approximately the same distance as the length of prongs 8a–c. Mechanical plunger 40 is moved to the fully extended lockout position when the predetermined number of sterilization/use cycles have been completed. When mechanical plunger 40 is moved to the fully extended lockout position, it can no longer be pushed into housing 2. In this configuration, mechanical plunger 40 physically inhibits connection of prongs 8a–c to a power source (not shown), thereby preventing further use of electrosurgical apparatus 1. When mechanical plunger 40 is in the fully extended position, window 6 allows the user to view indicator 22 and ascertain that there are no remaining uses left of electrosurgical apparatus 1.

As will be appreciated by those skilled in the art, a variety of types and configurations of counter/lockout mechanisms can be utilized without departing from the scope and spirit of the present invention. For example, in one embodiment the mechanical plunger of the lockout mechanism can be extended from the housing at two or more different amounts of extension. In another embodiment, the plunger can be extended from the housing a single amount of extension that operates to both decrement the indicator and provide lockout functionality. In another embodiment, a first mechanism is utilized as a mechanically actuated element to decrement the counter and a second mechanism is utilized as a lockout mechanism. In other embodiments, the plunger can be extended from the housing a distance either greater or lesser than the length of the prongs.

The illustrated configuration of indicator 22 allows a user to monitor the number of remaining uses before electrosurgical apparatus 1 should be discarded. By showing the number of remaining uses, the user is provided adequate opportunity to obtain a replacement electrosurgical apparatus 1 before a procedure is to be performed. As will be appreciated by those skilled in the art, a variety of types and configurations of counter/lockout mechanisms can be utilized without departing from the scope and spirit of the present invention. For example, in one embodiment a counter/lockout mechanism can be utilized which impedes or prevents the flow of electrical current from the prongs to the power cord. In an alternative embodiment, a counter/lockout mechanism can prevent proper assembly of the components of a modularized electrosurgical apparatus prior to surgery once the predetermined number of sterilization/use cycles have been completed.

Figure 2:
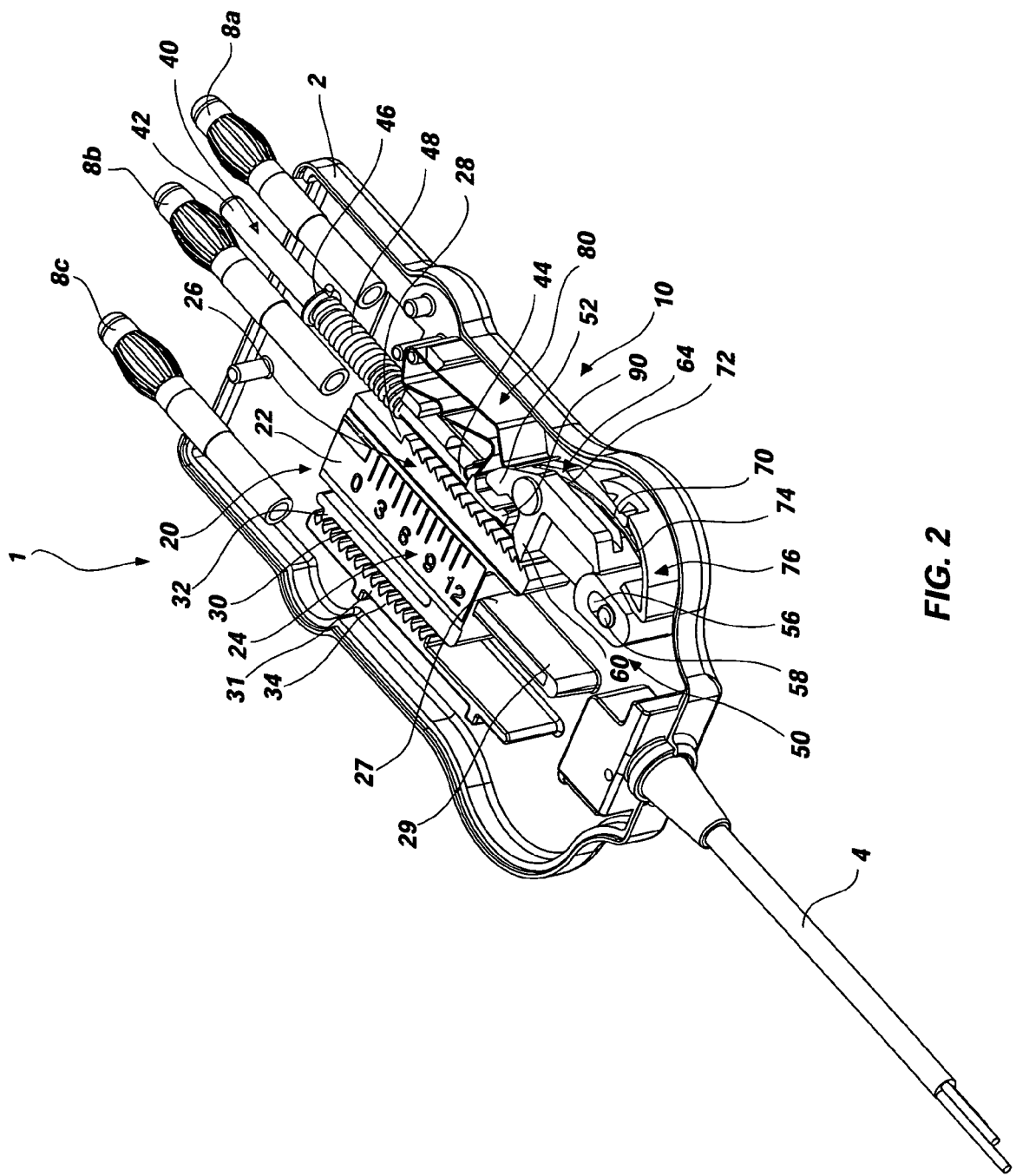
FIG. 2 is a perspective view of the embodiment shown in FIG. 1A, showing its internal components.

FIG. 2 is a perspective internal view of electrosurgical apparatus 1 illustrating a counter/lockout mechanism 10 according to one embodiment of the present invention. In the illustrated embodiment, counter/lockout mechanism 10 includes an indicator assembly 20, a mechanical plunger 40, a bias spring 48, an actuator 50, a temperature actuated element 70, a spring 80, and an actuator engagement member 90.

Indicator assembly 20 includes indicator 22. In the illustrated embodiment, indicator 22 illustrates to the user the number of sterilization/use cycles remaining before the electrosurgical apparatus 1 should be discarded. Actuator 50 cooperatively engages indicator 22 such that operation of actuator 50 results in a single decrement of indicator 22 for each sterilization/use cycle that is conducted.

Proper operation of actuator 50 is facilitated by a mechanically actuated element (i.e. mechanical plunger 40) and a temperature actuated element 70. Mechanical plunger 40 is actuated during each use of electrosurgical apparatus 1. Temperature actuated element 70 operates in connection with each sterilization cycle that is conducted. The combination of mechanical plunger 40 and temperature actuated element 70 results in a single actuation of actuator 50 for each sterilization/use cycle that is conducted. In one embodiment, temperature actuated element 70 and mechanical plunger 40 cooperatively move actuator 50 in a first and second direction. This allows actuator 50 to move indicator 22 and effectuate a change of one or a plurality of indicia to show that a sterilization/use cycle has been completed.

In the illustrated embodiment, mechanical plunger 40 comprises a pin or rod and includes a proximal end 42 and a distal end 44. Proximal end 42 is positioned between prong 8a and prong 8b and can selectively be moved between an extended position and a depressed position. Distal end 44 of mechanical plunger 40 is positioned adjacent actuator 50 and indicator 22 (see FIG. 3A) and is configured to both engage actuator 50 to move indicator 22. Depression of mechanical plunger 40 results in movement of actuator 50. In the illustrated embodiment, proximal end 42 of mechanical plunger 40 is in an extended position. As mechanical plunger 40 is biased distally, distal end 44 of mechanical plunger 40 engages actuator 50. This causes movement of actuator 50 in the distal direction.

In the illustrated embodiment, temperature actuated element 70 is a shape memory alloy, such as, but not limited to, Nitinol®. When temperature actuated element 70 is subjected to sufficient temperatures, it returns to an original shape and is rigid and difficult to bend. Thus, as electrosurgical apparatus 1 undergoes a sterilization cycle, temperature actuated element 70 changes from a curved configuration to the illustrated more linear configuration resulting from stiffening of temperature actuated element 70. Stiffening of temperature actuated element 70 pushes actuator 50 in the direction of prongs 8a–c. This causes actuator 50 to be displaced relative to indicator 22. Temperature actuated element 70 is one example of a means for detecting a temperature above ambient. A variety of types and configurations of means for detecting a temperature above ambient can be utilized without departing from the scope and spirit of the present invention. For example, in one embodiment a temperature actuated element that includes magnetic properties that vary with temperature can be utilized. In another embodiment, a temperature actuated element including a liquid portion, or liquid filled portion, that is responsive to temperature fluctuations can be utilized.

Bias spring 48 circumscribes mechanical plunger 40. Bias spring 48 biases mechanical plunger 40 in the proximal direction such that mechanical plunger 40 extends from housing 2 when proximal end 42 of mechanical plunger 40 is not contacted by a wall, socket, or other surface. Spring 80 facilitates the lockout position of mechanical plunger 40 when a predetermined number of sterilization/use cycles have been conducted. Actuator engagement member 90 facilitates lateral movement of actuator 50 to ensure that a single decrement of indicator 22 occurs for each actuation of actuator 50. Additionally, actuator engagement member 90 interacts with mechanical plunger 40 to maintain a desired path of movement of mechanical plunger 40 while controlling extension of mechanical plunger 40 until the desired number of sterilization/use cycles have been conducted.

Figure 3A:
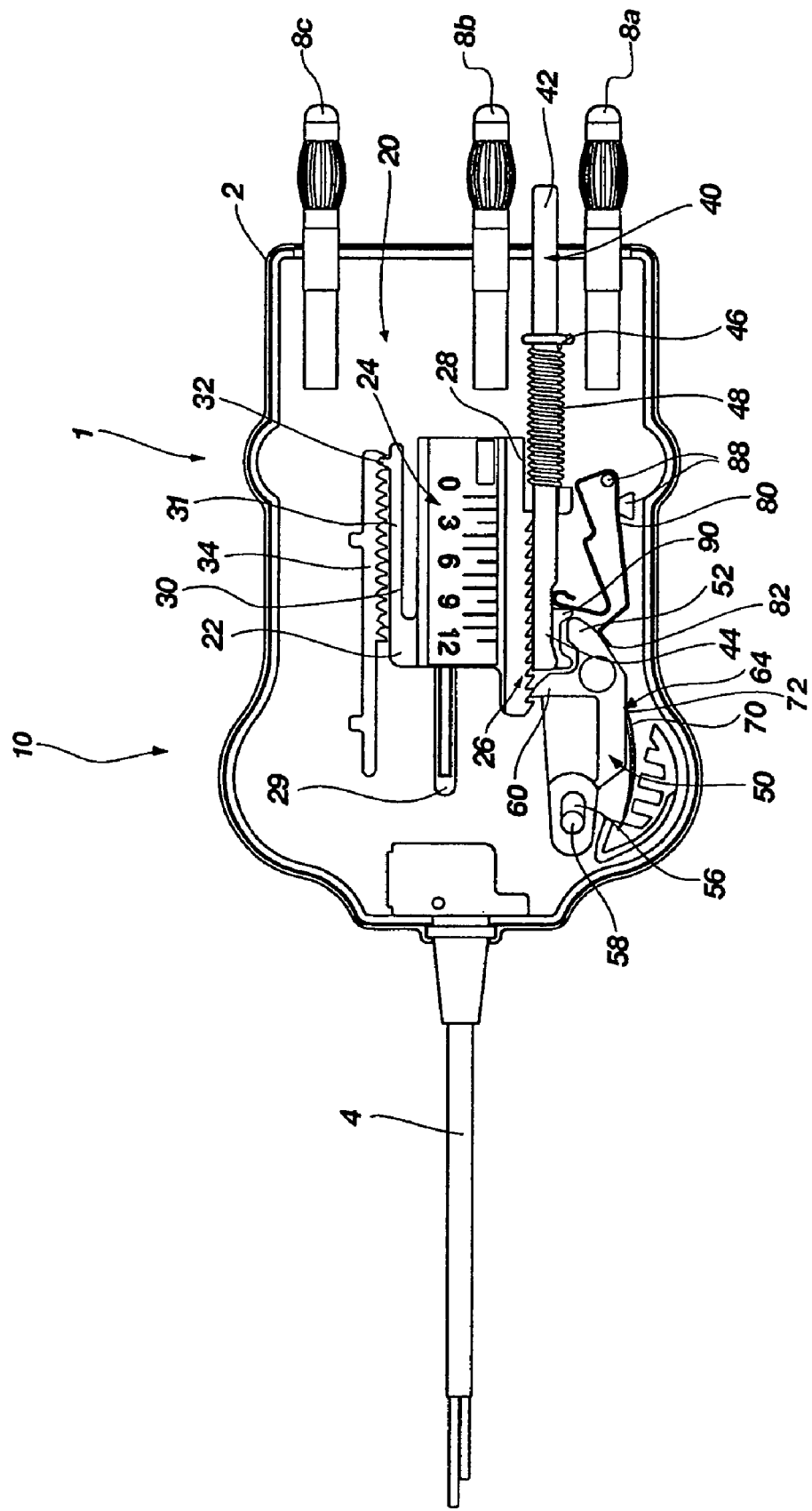
FIG. 3A is a top internal view of the embodiment shown in FIG. 1A, illustrating the counter/lockout mechanism before a first use cycle has been conducted.

FIG. 3A is a top internal view of electrosurgical apparatus 1 illustrating the juxtaposition of the components of counter/lockout mechanism 10 according to one embodiment of the present invention. In the illustrated embodiment, counter/lockout mechanism 10 is shown prior to a first use of electrosurgical apparatus 1. In the illustrated embodiment, indicator assembly 20 is shown. Indicator assembly 20 includes indicator 22, a guide 29, a pawl spring 30, and a securement member 34. Indicator 22 illustrates to the user the number of sterilization/use cycles remaining before electrosurgical apparatus 1 should be discarded.

In the illustrated embodiment, indicator 22 comprises indicia 24, teeth 26, guide slot 27 (see FIG. 2), and lockout portion 28. Indicia 24 are positioned on an upper surface of indicator 22. In the illustrated embodiment, indicia 24 include a plurality of lines and associated reference numerals. The plurality of lines and associated reference numerals represent the number of remaining uses before electrosurgical apparatus 1 should be discarded. The positioning of indicator 22 is selected such that the appropriate indicium (line and associated reference numeral) is positioned to be viewed through window 6 (see FIG. 1) when the corresponding number of remaining uses have yet to be conducted (see FIGS. 1A–1C). As indicator 22 moves from its proximal position, to its distal position, the one or plurality of indicia viewed through window 6 (FIG. 1) also change. In the illustrated embodiment, movement of indicator 22 in the distal direction decrements the counter.

Teeth 26 cooperatively interact with actuator 50 to move indicator 22 in the distal direction. The number, dimensions, and positioning of teeth 26 are selected to allow decrementing of a single indicium of indicia 24 for each sterilization/use cycle that has been conducted. In the illustrated embodiment, the distal extension of teeth 26 relative to the body of indicator 22 facilitates placement of actuator 50 in a more distal position relative to indicator 22. As shown in FIG. 2, a guide slot 27 is positioned on the underside of indicator 22 to receive guide 29. The cooperative interaction of guide slot 27 and guide 29 allows for smooth and predictable movement of indicator 22 as indicator moves from a proximal position to a more distal position.

Returning to FIG. 3A, lockout portion 28 is positioned adjacent mechanical plunger 40 in the proximal corner of indicator 22. Lockout portion 28 is configured to allow mechanical plunger 40 to move in a lateral direction away from actuator engagement member 90 when indicator 22 is moved to its distal most position. Pawl spring 30 is secured to indicator 22. Pawl spring 30 cooperates with securement member 34 to minimize inadvertent movement of indicator 22. Pawl spring 30 includes a resilient arm 31 and a pawl spring engagement tooth 32. Resilient arm 31 flexes to allow pawl spring engagement tooth 32 to move relative to the teeth of securement member 34. Pawl spring engagement tooth 32 is configured to be positioned between individual sets of teeth of securement member 34 or otherwise engage one or more teeth, or spaces between adjacent teeth, of securement member 34 to minimize inadvertent movement of indicator 22. When actuator 50 causes movement of indicator 22, resilient arm 31 is sufficiently flexible to allow movement of pawl spring engagement tooth 32 away from securement member 34 in the direction of indicator 22. This allows pawl spring engagement tooth 32 to move from the position between a first set of teeth, over the distal tooth of the first set of teeth, and between a second set of teeth. In the illustrated embodiment, pawl spring engagement tooth 32 is positioned between the first set of teeth. This is because electrosurgical apparatus 1 has not undergone a first use cycle and mechanical plunger 40 has not yet been depressed during a first use cycle.

As will be appreciated by those skilled in the art, a variety of types and configurations of indicators can be utilized without departing from the scope and spirit of the present invention. For example, in one embodiment the indicator includes a seven segment display that illustrates the number of remaining uses before the electrosurgical apparatus should be discarded. In another embodiment, the indicator includes a circular member. In another embodiment, the indicator is gear driven. In another embodiment, the indicator includes a digital display.

With continued reference to FIG. 3A, actuator 50 cooperatively engages indicator 22 to result in rearward movement of indicator 22. In the illustrated embodiment, actuator 50 includes a projection 52, a cam slot 56, an indicator engagement tooth 60, and a slot 64 which is depicted in more detail in FIG. 2. Projection 52, as shown in FIG. 3A, interacts with actuator engagement member 90 to facilitate pivoting movement of actuator 50. Cam slot 56 interacts with pin 58 to cause a rearward movement of actuator 50 while also allowing pivoting movement of actuator 50 in response to depression of mechanical plunger 40. The pivoting movement of actuator 50 allows actuator 50 to move indicator 22 a single decrement despite the difference in the distance of movement of mechanical plunger 40 and the distance of movement of indicator 22 subsequent to a single sterilization/use cycle.

Indicator engagement tooth 60 engages teeth 26 of indicator 22 during the initial rearward movement of actuator 50. As the proximal portion of actuator 50 begins to pivot in a lateral direction during movement of actuator 50 toward power cord 4, indicator engagement tooth 60 disengages from teeth 26 of indicator 22. Once indicator engagement tooth 60 disengages from teeth 26, additional rearward movement of indicator 22 stops.

In the illustrated embodiment, a first end 82 of spring 80 contacts projection 52 of actuator 50 and is maintained in the desired position through support structures 88 formed in housing 2. When mechanical plunger 40 is not positioned between actuator 50 and indicator 22, first end 82 of spring 80 biases projection 52 toward indicator 22 positioning projection 52 adjacent actuator engagement member 90. Actuator 50 includes a slot 64 (see also FIG. 2). Slot 64 accommodates proximal end 72 of temperature actuated element 70. Slot 64 facilitates assembly of lockout/counter mechanism 10 by allowing the temperature actuated element 70 to be simply and efficiently positioned relative to actuator 50. The configuration of slot 64 and temperature actuated element 70 provides for desired movement of actuator 50 in response to a sterilization cycle without requiring overly precise engineering or assembly of the components of the counter/lockout assembly 10.

Figure 3B:
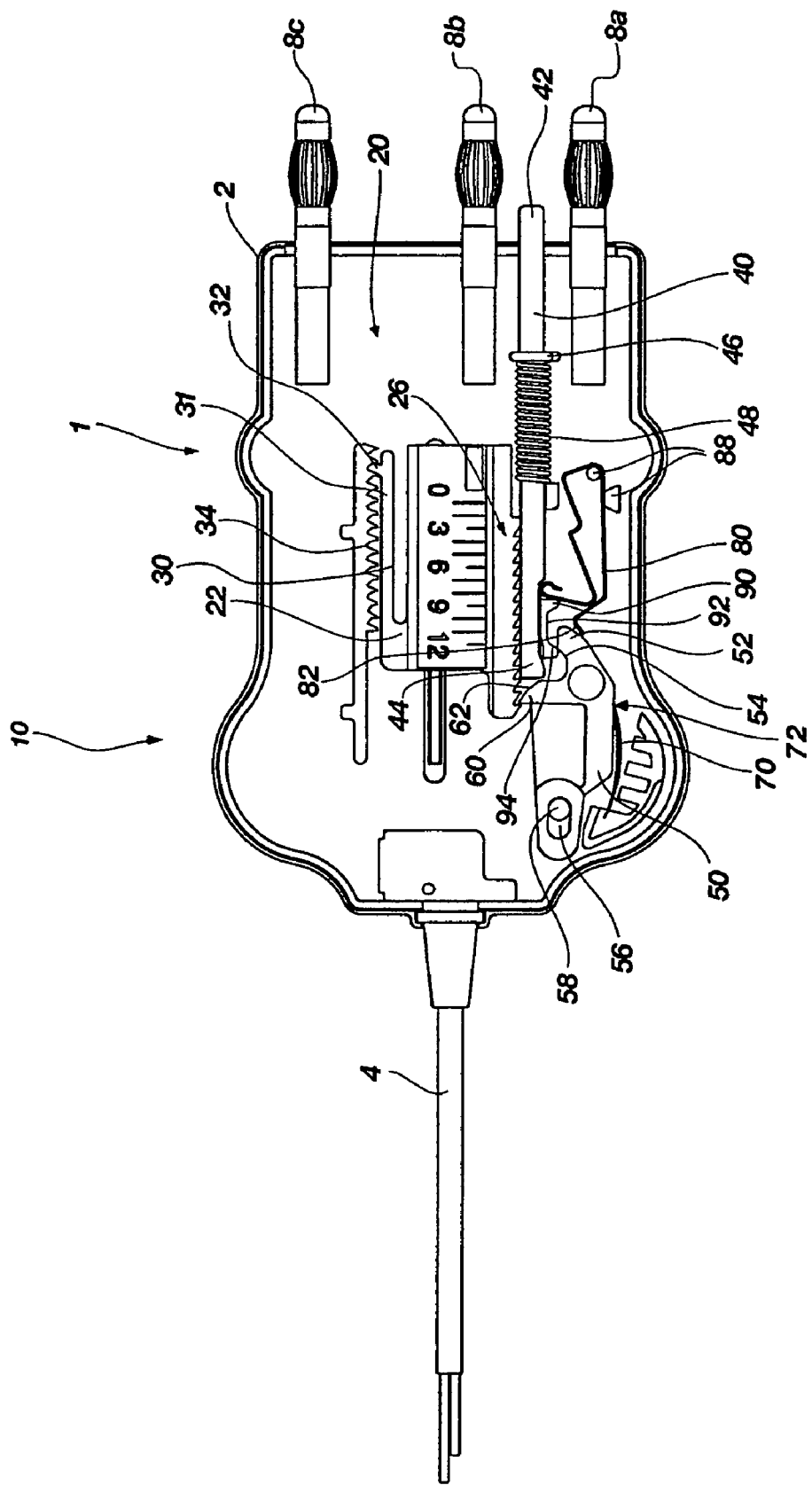
FIG. 3B is a top internal view of the embodiment shown in FIG. 1A, showing the mechanical plunger of the counter/lockout mechanism in a partially depressed position.

Operation of actuator 50 will be discussed in greater detail with reference to FIG. 3B–4B. FIG. 3B is a top internal view of electrosurgical apparatus 1 illustrating movement of actuator 50 in response to a partial depression of mechanical plunger 40. In the illustrated embodiment, proximal end 42 of mechanical plunger 40 has been moved in the distal direction but not to the extent that the entire length of mechanical plunger 40 is positioned internal to housing 2. As mechanical plunger 40 is biased distally, distal end 44 of mechanical plunger 40 engages actuator 50. This causes movement of actuator 50 in the distal direction. As actuator 50 moves in the distal direction, indicator engagement tooth 60 engages one of teeth 26 of indicator 22. With the engagement of actuator 50 and indicator engagement tooth 60, indicator 22 moves in the distal direction as actuator 50 moves distally. When indicator 22 is moved a predetermined distance in the distal direction a change of indicia is effectuated. The change of indicia shows to the user the number of remaining uses subsequent to the completed sterilization/use cycle. In the illustrated embodiment, a change of indicia and movement of pawl spring engagement tooth 32 occurs with the first 0.06 inches of movement of actuator 50.

As mechanical plunger 40 is depressed further into the housing of electrosurgical apparatus 1 (moves from the position of FIG. 3B to position of FIG. 3C), pivoting of actuator 50 away from indicator 22 prevents additional rearward movement of indicator 22. In FIG. 3B, the proximal portion of actuator 50 has begun to pivot away from teeth 26 of indicator 22. However, indicator engagement tooth 60 has not yet separated from teeth 26. The pivoting movement of actuator 50 away from indicator 22 is facilitated by the configuration of projection 52 and actuator engagement member 90. Before mechanical plunger 40 is depressed, projection 52 is positioned in trough 92 of actuator engagement member 90 as shown in FIG. 3A. When mechanical plunger 40 begins to move actuator 50 in a rearward direction, as shown in FIG. 3B, lateral displacement surface 54 of projection 52 contacts lateral displacement surface 94 of actuator engagement member 90. The interaction between lateral displacement surface 54 and lateral displacement surface 94 causes an initial degree of pivoting of projection 52 away from indicator 22.

Once the initial degree of pivoting of projection 52 occurs, distal end 44 of mechanical plunger 40 begins to contact ramp surface 62 of indicator engagement tooth 60. As distal end 44 of mechanical plunger 40 is pushed in a distal direction it slides along the length of ramp surface 62. This results in additional pivoting and lateral displacement of projection 52 away from indicator 22. Lateral displacement of projection 52 also results in lateral movement of indicator engagement tooth 60. The configuration of cam slot 56 and pin 58 allows the pivoting movement of actuator 50 that is facilitated by (a) the interaction of lateral displacement surfaces 54 and 94, and (b) the interaction between distal end 44 of mechanical plunger 40 and ramp surface 62 of indicator engagement tooth 60.

The configuration of teeth 26 of indicator 22 and the manner in which indicator engagement tooth 60 is positioned relative to teeth 26 prevents multiple decrements of indicator 22 when mechanical plunger 40 is partially depressed multiple times. Where mechanical plunger 40 is depressed sufficiently to cause a decrement of indicator 22, actuation of temperature actuated element 70 is required before a subsequent depression of mechanical plunger 40 will cause an additional decrement of indicator 22. As a result, the user may plug or unplug prongs 8a–c, or otherwise depress mechanical plunger 40, multiple times without decrementing indicator 22.

Figure 3C:
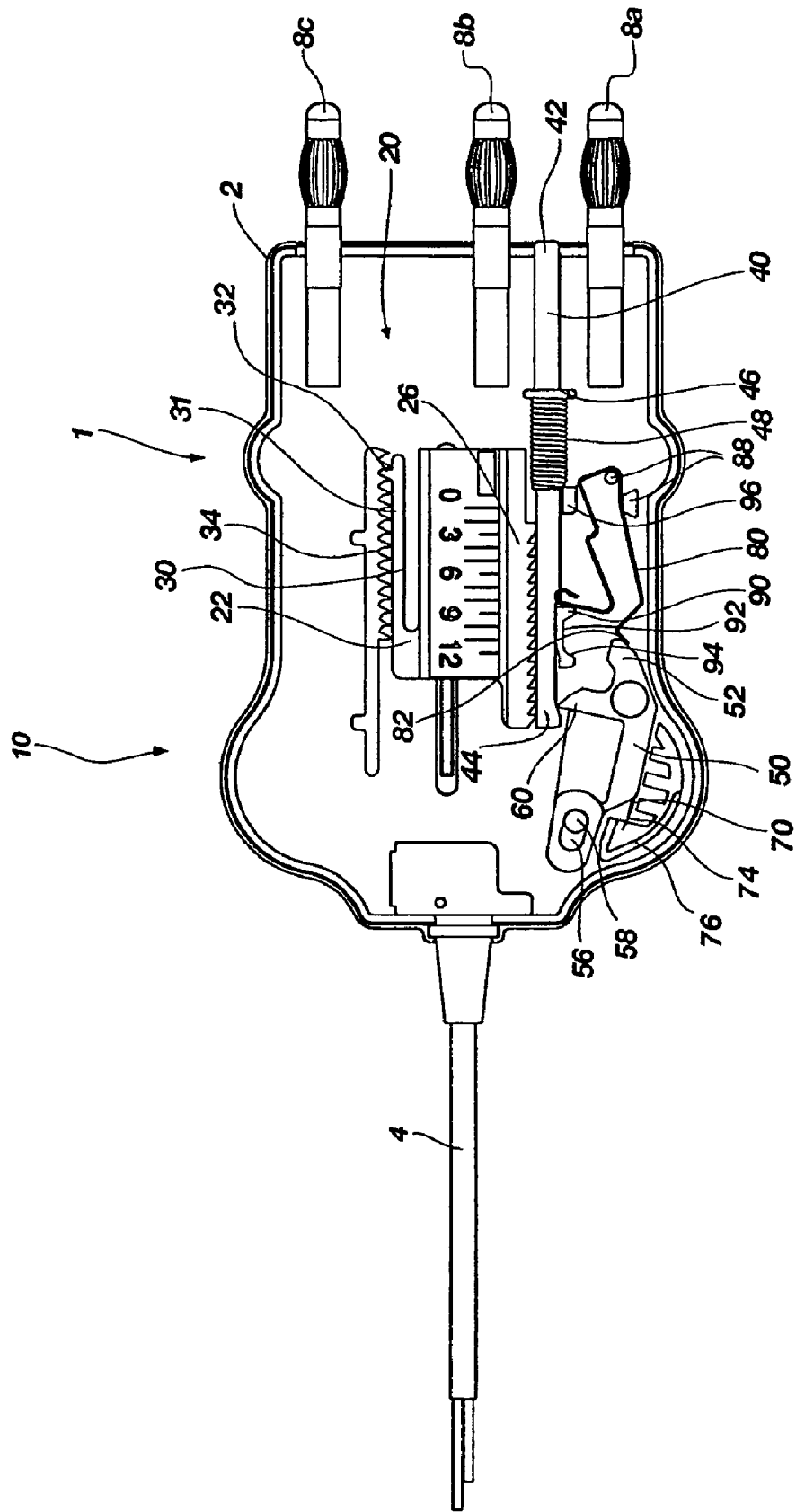
FIG. 3C is a top internal view of the embodiment shown in FIG. 1A, showing the mechanical plunger of the counter/lockout mechanism in a fully depressed position.

FIG. 3C is a top internal view of electrosurgical apparatus 1 in which mechanical plunger 40 is completely depressed into housing 2. The pivoting of actuator 50 results in disengagement of indicator engagement tooth 60 from teeth 26 of indicator 22. Additional rearward movement of actuator 50 and/or mechanical plunger 40 causes no further movement of indicator 22 because of the disengagement of indicator engagement tooth 60 from the teeth of indicator 22. Movement of distal end 44 of mechanical plunger 40 between indicator engagement tooth 60 and teeth 26 maintains separation between actuator 50 and indicator 22.

The pivoting movement of actuator 50 allows actuator 50 to decrement indicator 22 a single position despite the difference in the distance of movement of mechanical plunger 40 and the distance of movement of indicator 22. In one embodiment, mechanical plunger 40 is depressed approximately 0.25 inches during each actuation of mechanical plunger 40. In the embodiment, indicator 22 is moved only 0.060 inches as a result of each actuation of mechanical plunger 40. As will be appreciated by those skilled in the art, the amount of movement of the mechanical plunger relative to the amount of movement of indicator can vary without departing from the scope and spirit of the present invention. In one embodiment the plunger can be moved between 0.01 inches and 0.75 inches. In another embodiment, the indicator can be moved between 0.02 inches and 0.125 inches. In yet another embodiment, the distance of movement of the plunger is greater than the amount of movement of the indicator. In another embodiment, the amount of movement of the plunger and the indicator is at least in part dependent on the size of the electrosurgical lockout mechanism and the housing containing the electrosurgical lockout mechanism. Additionally, a variety of types and configurations of actuators can be utilized without departing from the scope and spirit of the present invention.

As actuator 50 is moved in the distal direction, force is exerted on temperature actuated element 70 increasing the degree of curvature of temperature actuated element 70. The increased degree of curvature of temperature actuated element 70 can be created when temperature actuated element 70 is not subject to the temperatures that result in the increased rigidity of temperature actuated element 70. As a result, temperature actuated element 70 provides minimal resistance allowing distal end 74 of temperature actuated element 70 to be moved closer to proximal end 72 (FIG. 2) of temperature actuated element 70. Because the position of distal end 74 of temperature actuated element 70 is maintained by seat 76, proximal end 72 (FIG. 2) of temperature actuated element 70 will move in the direction of distal end 74.

Once actuator 50 is disengaged from indicator 22, unplugging and subsequent insertion of the prongs into an outlet will not result in movement of indicator 22. This is due to the fact that indicator engagement tooth 60 is no longer in contact with indicator 22. Movement of mechanical plunger 40 in the direction of prongs 8a–c does not result in movement of actuator 50 in the direction of indicator 22 or the engagement of indicator 22 by indicator engagement tooth 60. As a result, a user may plug and unplug the prongs multiple times without decrementing indicator 22. As mechanical plunger 40 is depressed, a flange 46 is moved closer to bias spring contact member 96 causing compression of bias spring 48. The compression of bias spring 48 results in a biasing force on flange 46 in the direction opposite bias spring contact member 96 urging mechanical plunger 40 to return to its extended position whenever electrosurgical apparatus 1 is unplugged from the electrosurgical power source (not shown).

As a number of sterilization/use cycles are being conducted, indicator 22 will continue to move further and further in the direction of power cord 4. As indicator 22 moves further in the direction of power cord 4 one or a plurality of indicia 24 are displayed indicating to the user a change in the number of remaining sterilization/use cycles. As will be appreciated by those skilled in the art, a variety of types and configurations of lockout mechanisms can be utilized without departing from the scope and spirit of the present invention.

As previously discussed, in the embodiment illustrated in FIGS. 1–4B indicator 22 includes a pawl spring 30 that maintains consistent decrementing of indicator 22. Pawl spring 30 includes a resilient arm 31 that maintains contact between a pawl spring engagement tooth 32 of pawl spring 30 and the teeth of a securement member 34. In FIG. 3B, pawl spring engagement tooth 32 is positioned between the set of teeth immediately behind the set of teeth between which pawl spring engagement tooth 32 was positioned in FIG. 3A. This is because electrosurgical apparatus 1 has undergone a first use cycle which has resulted in movement of indicator 22.

As previously discussed, pawl spring 30 includes a resilient arm 31 that maintains contact between a pawl spring engagement tooth 32 and the teeth of a securement member 34. As indicator 22 is decremented, the force exerted on indicator 22 by actuator 50 results in movement of pawl spring engagement tooth 32. The engagement of pawl spring engagement tooth 32 and securement member 34 resists movement of indicator 22 until a threshold amount of force is exerted on indicator 22 through plunger 40 and actuator 50. This minimizes the possibility of inadvertent movement of indicator 22 in the absence of intentional depression of mechanical plunger 40. Intentional depression of mechanical plunger 40, such as that produced when inserting prongs 8a–c into an electrosurgical power source (not shown), is sufficient to exceed the threshold amount of force needed to move pawl spring engagement tooth 32 from a position between a first set of teeth of securement member 34, over one of the teeth, and into position between a second set of teeth. Additionally, the configuration of the teeth of securement member 34 resists movement of pawl spring engagement tooth 32 in the proximal direction while allowing movement of pawl spring engagement tooth 32 in the distal direction.

Pawl spring 30, pawl spring engagement tooth 32, and securement member 34 also maintain proper decrementing of indicator 22 by providing defined distances at which pawl spring engagement tooth 32 is positioned between depressions of mechanical plunger 40. As will be appreciated by those skilled in the art, a variety of types and configurations of mechanisms for minimizing inadvertent movement of the indicator can be utilized without departing from the scope and spirit of the present invention.

Figure 3D:
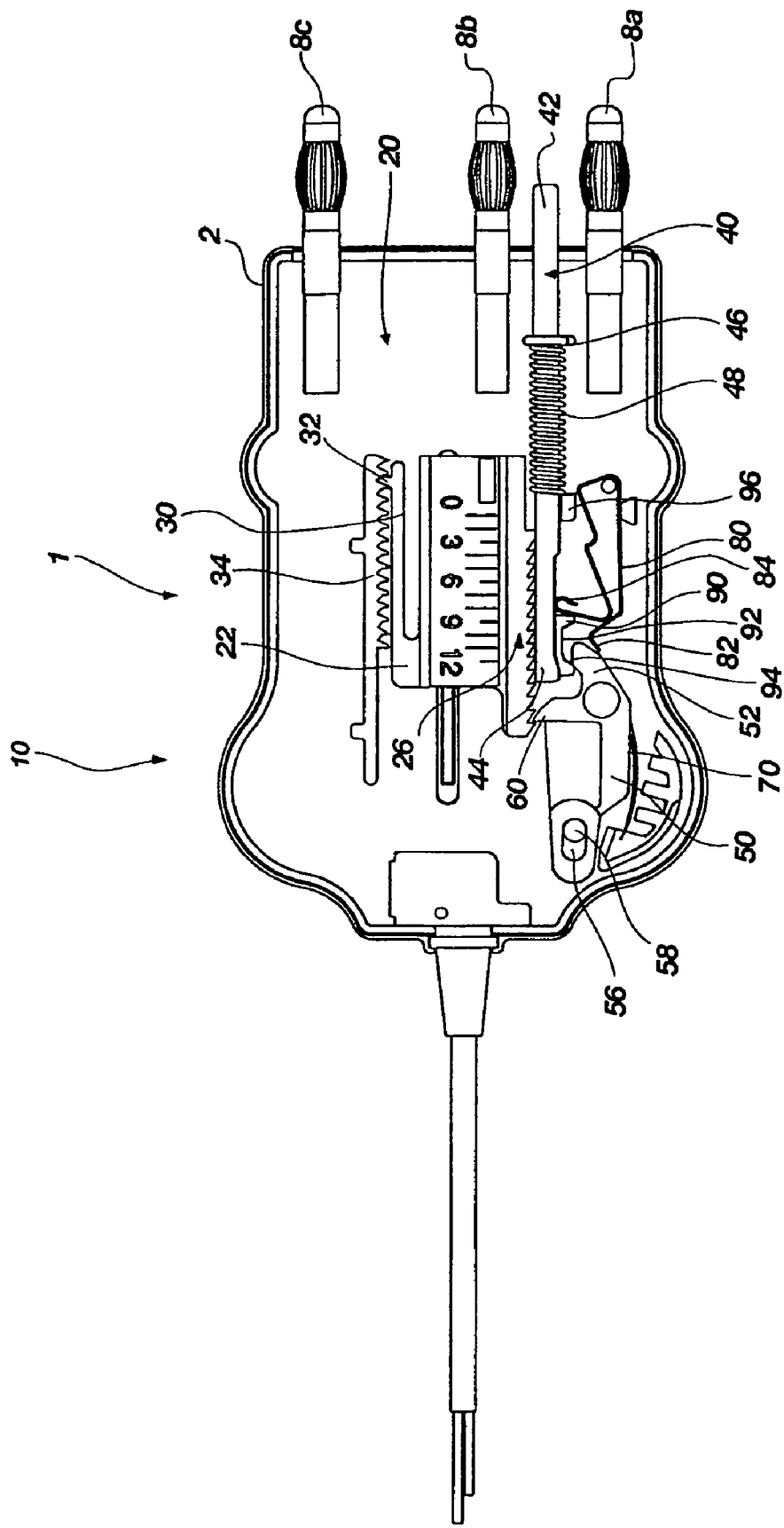
FIG. 3D is a top internal view of the embodiment shown in FIG. 1A, subsequent to the completion of a use cycle showing the mechanical plunger of the counter/lockout mechanism in a partially extended position.

Turning to FIG. 3D, illustrated is the operation of actuator 50 when mechanical plunger 40 is partially extended from housing 2 following use of electrosurgical apparatus 1 and before a subsequent sterilization cycle. FIG. 3D illustrates the position of the internal components of electrosurgical apparatus 1 when indicator 22 has been moved sufficiently to indicate to a user that the electrosurgical instrument has been used once.

As shown, spring 80 is positioned adjacent actuator 50 and mechanical plunger 40. Spring 80 is configured to maintain the proper function of components of counter/lockout mechanism 10. First end 82 of spring 80 contacts projection 52 of actuator 50. When mechanical plunger 40 is no longer positioned between indicator engagement tooth 60 and teeth 26 of indicator 22, spring 80 biases projection 52 of actuator 50 in the direction of indicator 22. In one embodiment, biasing of actuator 50 can facilitate engagement of indicator engagement tooth 60 with the teeth 26 of indicator 22. In another embodiment, actuation of temperature actuated element 70 is required to cause engagement of indicator engagement tooth 60 with teeth 26 of indicator 22.

When indicator 22 is not at its distal most displacement, indicator 22 contacts and provides lateral support along one side of at least a portion of mechanical plunger 40 adjacent to distal end 44 providing a counteracting force to second end 84 of spring 80. The counteracting forces of second end 84 of spring 80 and indicator 22 controls lateral movement of mechanical plunger 40. In the illustrated embodiment, distal end 44 of mechanical plunger 40 is slightly thicker than other portions of mechanical plunger 40. The cross-sectional thickness of distal end 44 is selected such that distal end 44 is wider than the width of the gap between teeth 26 and actuator engagement member 90 such that the inner surface of actuator engagement member 90 (i.e. the surface facing plunger 40) prevents movement of distal end 44 of mechanical plunger 40 past actuator engagement member 90.

Figure 4A:
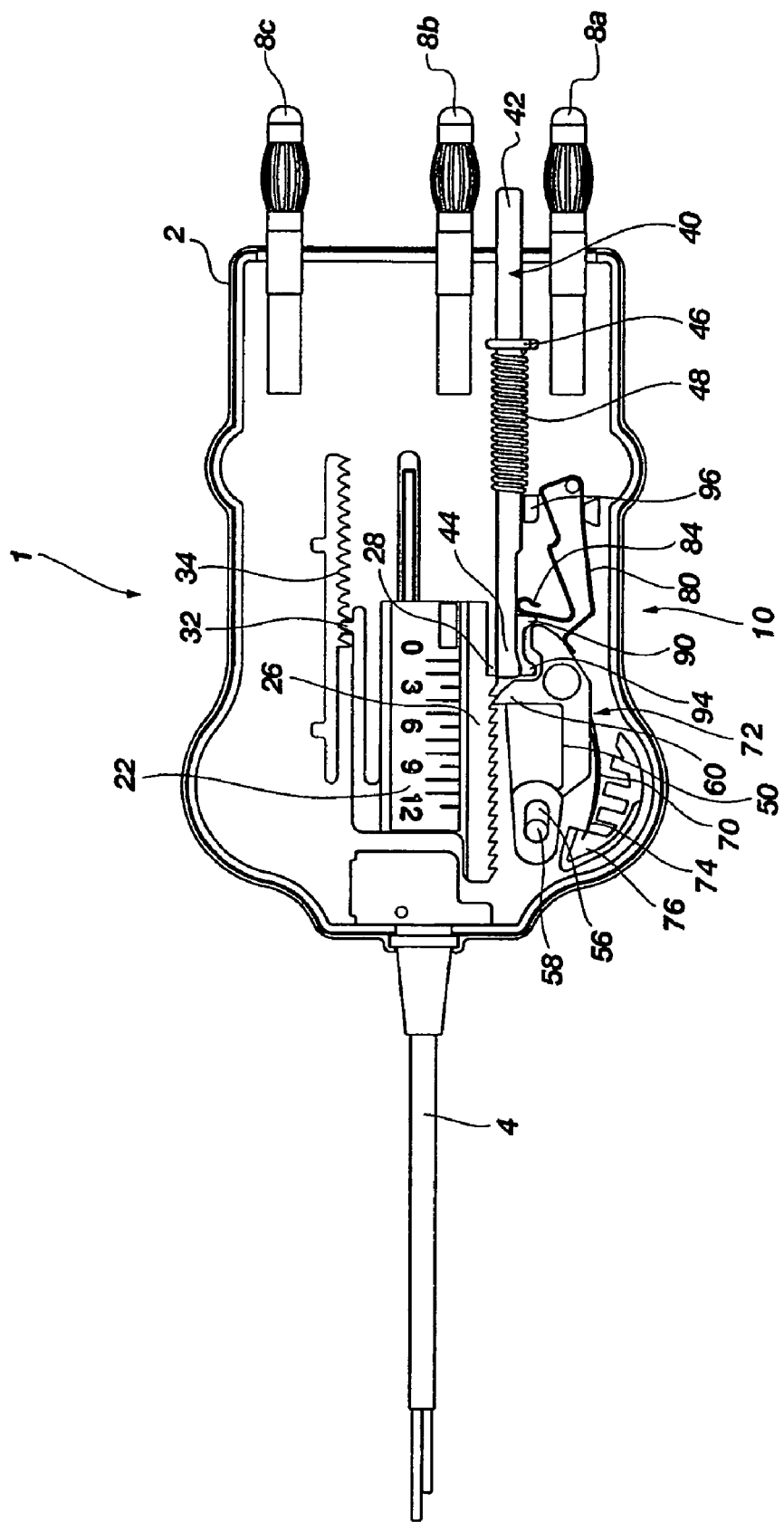
FIG. 4A is a top internal view of the embodiment shown in FIG. 1A, illustrating the position of a pawl spring and the mechanical plunger subsequent to a sterilization cycle, but before the final use cycle.

Turning to FIG. 4A, illustrated is a top internal view of electrosurgical apparatus 1 subsequent to actuation of temperature actuated element 70 but following a series of sterilization/use cycles. When actuated, temperature actuated element 70 returns actuator 50 to a position in which indicator engagement tooth 60 again engages teeth 26 of indicator 22. Actuation of temperature actuated element 70 prepares for decrementing of indicator 22. In the illustrated embodiment, temperature actuated element 70 engages actuator 50 such that temperature actuated element 70 remains in a non-linear configuration subsequent to being actuated. By remaining in a non-linear configuration, there is a decreased likelihood that temperature actuated element 70 will impede depression of mechanical plunger 40 when depression of mechanical plunger 40 is desired.

In FIG. 4A, temperature actuated element 70 includes a shape memory alloy, such as, but not limited to, Nitinol®. When the temperature actuated element 70 is subjected to sufficient temperatures, it returns to an original shape and is rigid and difficult to bend. Thus, as electrosurgical apparatus 1 undergoes a sterilization cycle, temperature actuated element 70 changes from a curved position (FIG. 3C) to a more linear configuration of FIG. 4A. The more linear configuration of temperature actuated element 70 results from stiffening of temperature actuated element 70. Stiffening of temperature actuated element 70 pushes actuator 50 in a direction toward prongs 8a–c until pin 58 contacts the distal end of cam slot 56. This causes actuator 50 to be displaced relative to indicator 22.

With reference to FIGS. 2 and 4A, temperature actuated element 70 is positioned in a seat 76 formed in housing 2 of electrosurgical apparatus 1. A distal end 74 of temperature actuated element 70 engages seat 76 to prevent movement of distal end 74 of temperature actuated element 70 in the direction of power cord 4. A proximal end 72 of temperature actuated element 70 engages actuator 50 at slot 64 (best shown in FIG. 2) formed in the side of actuator 50.

When temperature actuated element 70 is heated to a predetermined temperature (e.g. during a sterilization procedure), the stiffness of temperature actuated element 70 increases, the strength increases, and the flexibility decreases. Stiffening of temperature actuated element 70 reduces the degree of curvature of temperature actuated element 70. When temperature actuated element 70 is subjected to sufficient heat it changes from its substantially curved configuration (FIG. 3C) to a more linear and rigid configuration, causing proximal end 72 to push the actuator 50 in the direction of prongs 8a–c, as shown in FIG. 4A.

In FIG. 4A, temperature actuated element 70 provides a pushing motion to move actuator 50. By utilizing a pushing motion, temperature actuated element 70 reduces the cost and complexity of manufacturing counter/lockout mechanism 10 while improving reliability of the system. This is due to the fact that stiffening of temperature actuated element 70 effectively moves actuator 50 without requiring precise engineering of the size, thickness, and length of temperature actuated element 70. This reduces the cost of designing and manufacturing temperature actuated element 70. Additionally, temperature actuated element 70 need not be integrally coupled to other components of the counter/lockout mechanism 10 to maintain the tolerances that can be required in pull type actuated devices. Instead, temperature actuated element 70 can easily be positioned in seat 76 and slot 64 (see FIG. 2) during assembly, substantially reducing the complexity, cost, and difficulty of assembling counter/lockout mechanism 10. As will be appreciated by those skilled in the art, a variety of types and configurations of temperature actuated elements can be utilized without departing from the scope and spirit of the present invention. In one embodiment, the temperature actuated element is configured to provide a pulling force to cause proper actuation of the indicator.

With continued reference to FIG. 4A, due to the configuration of teeth 26 of indicator 22 and indicator engagement tooth 60 of actuator 50, movement of actuator 50 in the direction of prongs 8a–c does not result in movement of indicator 22. Additionally, repeated heating and cooling of temperature actuated element 70 will not result in multiple decrements of the counter, as movement of indicator 22 only occurs in response to depression of mechanical plunger 40. As a result, actuator 50 does not effectuate a change of the one or a plurality of indicia 24 until both temperature actuated element 70 has experienced a sterilization cycle moving actuator 50 in one direction and mechanical plunger 40 has experienced a use cycle as indicated by depression of the plunger moving the actuator 50 in the opposite direction.

Figure 4B:
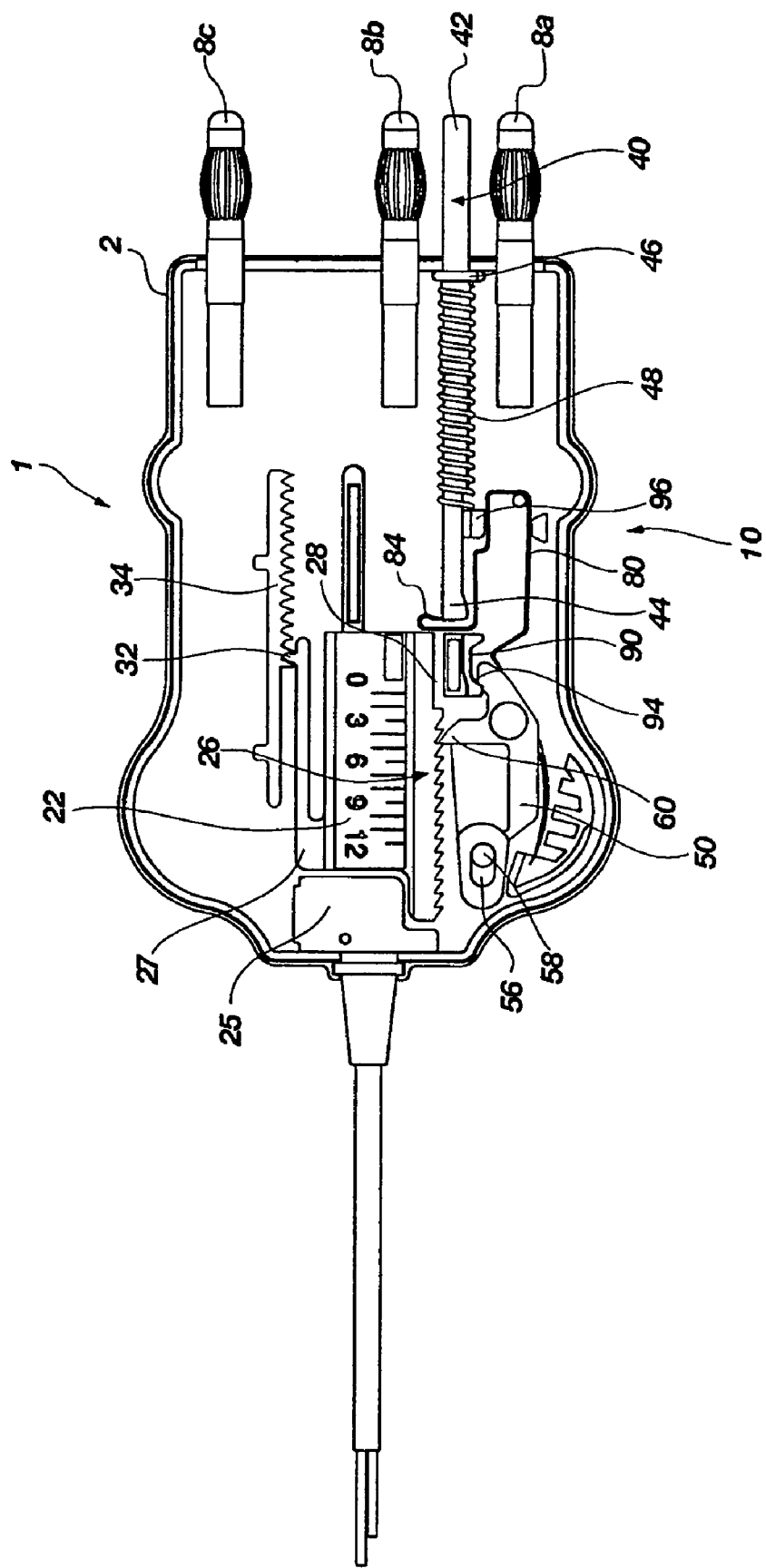
FIG. 4B is a top internal view of the embodiment shown in FIG. 1A, illustrating the mechanical plunger in a fully extended lockout position subsequent to the final use cycle.

FIG. 4B is a top internal view of electrosurgical apparatus 1 illustrating the position of various internal components of electrosurgical apparatus 1 following a sterilization cycle that exceeds the recommended number of sterilizations. As shown, spring 80 and indicator 22 cooperatively secure mechanical plunger 40 in an extended position. In the illustrated embodiment, indicator 22 has completed its final decrement and is no longer in contact with the distal end 44 of mechanical plunger 40. When indicator 22 is no longer in contact with the distal end 44 of mechanical plunger 40, it no longer provides lateral support for, and a counteracting force to oppose, second end 84 of spring 80. As a result, second end 84 of spring 80 contacts and biases distal end 44 of mechanical plunger 40 into lockout portion 28 of indicator 22. This allows distal end 44 to move past actuator engagement member 90 and allows mechanical plunger 40 to move to a fully extended lockout position as shown in FIG. 4B.

Mechanical plunger 40 is moved to the fully extended position utilizing bias spring 48. Before bias spring 48 moves mechanical plunger 40 to the fully extended position, bias spring 48 is compressed between flange 46 and bias spring contact member 96. Flange 46 is immovably coupled to mechanical plunger 40. Bias spring contact member 96 is integrally coupled to the lower portion of the housing 2.

When lockout portion 28 is positioned adjacent actuator engagement member 90 second end 84 of spring 80 biases distal end 44 of mechanical plunger 40 in the lateral direction. This provides additional distance between actuator engagement member 90 and indicator 22 such that the distance between actuator engagement member 90 and indicator 22 is greater than the width of distal end 44 of mechanical plunger 40. As a result, actuator engagement member 90 no longer contacts distal end 44 of mechanical plunger 40 in a way that can provide counteracting force to the exertion of bias spring 48 on flange 46. In the absence of a counteracting force being provided by contact with actuator engagement member 90, the force exerted by bias spring 48 on flange 46 results in movement of mechanical plunger 40 in the proximal direction. In one embodiment of the present invention, bias spring contact member and actuator engagement member are integrally formed from the lower portion of housing. In an alternative embodiment, bias spring contact member and actuator engagement members are immovably affixed to one or more portions of housing 2.

In the illustrated embodiment, proximal movement of mechanical plunger 40 is stopped when flange 46 contacts an inner surface of housing 2. When flange 46 contacts the inner surface of housing 2, mechanical plunger 40 is fully extended from housing 2. Second end 84 of spring 80 contacts indicator 22 to secure mechanical plunger 40 in an extended position. Indicator 22 is positioned at its greatest distal displacement and is positioned in contact with stop 25. Stop 25 is formed from the lower portion of housing 2. Stop 25 prevents additional rearward displacement of indicator 22.

The configuration and positioning of indicator 22, second end 84, and distal end 44 of mechanical plunger 40 prevents depression of mechanical plunger 40. In the illustrated position, mechanical plunger 40 is at its greatest displacement from housing 2. By preventing depression of mechanical plunger 40, engagement of prongs 8a–c with a power source (not shown) is prevented. In this manner, counter/ lockout mechanism 10 impedes the user from utilizing electrosurgical apparatus 1 once a predetermined number of sterilization/use cycles have been completed. In the illustrated embodiment, pawl spring engagement tooth 32 is positioned between the final set of teeth of securement member 34. This is because the electrosurgical apparatus 1 has undergone the predetermined number of sterilization/use cycles and indicator 22 is positioned at its distal most displacement.

As will be appreciated by those skilled in the art, a variety of types and configurations of lockout mechanisms can be utilized without departing from the scope and spirit of the present invention. For example, in one embodiment the lockout mechanism utilizes a lateral biasing mechanism comprising a leaf spring. In another embodiment, the lockout mechanism utilizes a lateral biasing mechanism that does not include a leaf spring. In another embodiment, the lockout mechanism does not utilize a lateral biasing mechanism. In yet another embodiment, the lockout mechanism does not include a lockout portion.

Figure 5:
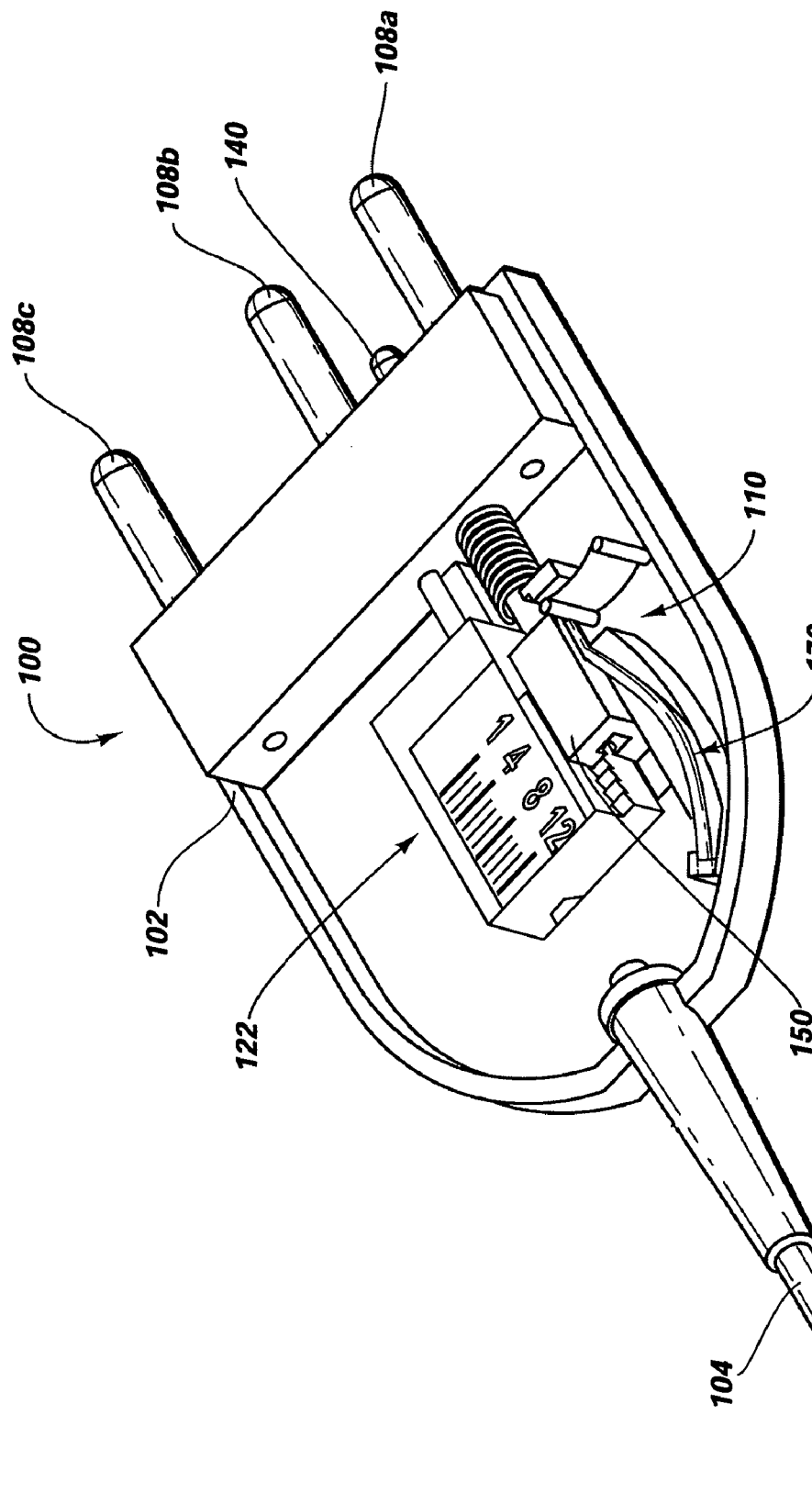
FIG. 5 is an internal perspective view of another exemplary embodiment of the counter/lockout mechanism according to the present invention.

FIG. 5 is an internal view of an electrosurgical apparatus 100 illustrating a counter/lockout mechanism 110 according to another embodiment of the present invention. To aid with explanation of the structures and functions of electrosurgical apparatus 100 and lockout/counter mechanism 110, the wires or other electrical connections from power cord 104 to prongs 108*a–c* have not been shown in FIGS. 5–9.

In the illustrated embodiment, counter/lockout mechanism 110 includes an indicator 122, an actuator 150, a temperature actuated element 170, and a mechanical plunger 140. Temperature actuated element 170 and mechanical plunger 140 cooperatively move actuator 150 in a first and second direction. This allows actuator 150 to move indicator 122 and effectuate a change of one or a plurality of indicia to show that a sterilization/use cycle has been completed.

In the illustrated embodiment, temperature actuated element 170 is a shape memory alloy, such as, but not limited to, Nitinol®. When the temperature actuated element 170 is subjected to sufficient temperatures, it returns to its original shape and is rigid and difficult to bend. Thus, as electrosurgical apparatus 100 undergoes a sterilization cycle, temperature actuated element 170 changes from its illustrated curved position to a more linear configuration resulting from stiffening of temperature actuated element 170 (as shown in FIG. 8). Stiffening of temperature actuated element 170 pushes actuator 150 in the direction of prongs 108*a–c*. This causes actuator 150 to be displaced relative to indicator 122.

Temperature actuated element 170 is one example of a means for detecting a temperature above ambient. A variety of types and configurations of means for detecting a temperature above ambient can be utilized without departing from the scope and spirit of the present invention. For example, in one embodiment a temperature actuated element that includes magnetic properties that vary with temperature are utilized. In another embodiment, a temperature actuated element including a liquid, or liquid filled, portion that is responsive to temperature fluctuations is utilized.

Subsequent to a sterilization cycle, when the user attempts to use electrosurgical apparatus 100, such as by plugging prongs 108*a–c* into an electrosurgical outlet (not shown), the proximal end of mechanical plunger 140 will be contacted and urged inside housing 102. Actuator 150 circumscribes a portion of mechanical plunger 140. The portion of mechanical plunger 140 positioned internal to actuator 150 engages an internal surface of actuator 150. As a result, when mechanical plunger 140 is moved in the direction of power cord 104 actuator 150 is moved in the direction of power cord 104. In other words, as mechanical plunger 140 is forced inside housing 102, actuator 150 is pushed in the direction of power cord 104. When actuator 150 is pushed in the direction of power cord 104, a surface on actuator 150 engages a complementing surface of indicator 122 causing indicator 122 to move in direction of power cord 104. Movement of indicator 122 effectuates a change in the position of the indicia indicating that a sterilization/use cycle has been completed. This also results in a decrement in the remaining number of uses of electrosurgical apparatus 100.

When an external force is no longer exerted on the proximal end of mechanical plunger 140, a bias spring can extend mechanical plunger 140 from housing 102. This results in the proximal end of mechanical plunger 140 being extended from housing 102. However, actuator 150 is not moved in the direction of prongs 108*a–c* until temperature actuated element 170 is actuated in response to a sterilization cycle. As a result, additional depression of mechanical plunger 140 does not result in movement of actuator 150, and movement of indicator 122, until a subsequent sterilization cycle has been conducted. Mechanical plunger 140 is one example of a means for detecting a use cycle. Other such means for detecting are known to those skilled in the art. For instance software with a chip, electrical lights, bar graphs, and a removable plunger that acts as a key for subsequent uses can be utilized as a means for detecting a use cycle.

Figure 6A:
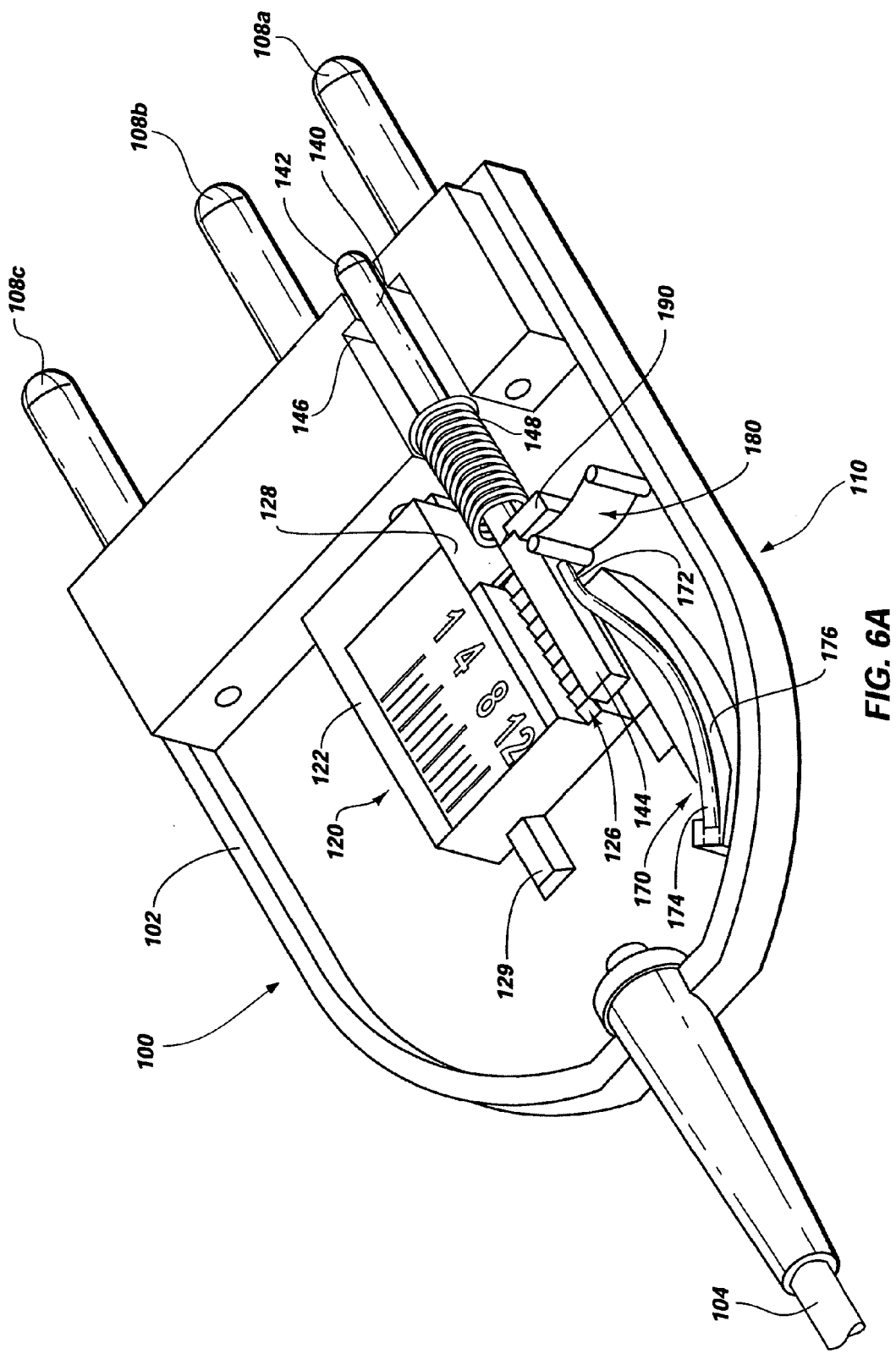
FIG. 6A is a partial perspective view of the embodiment shown in FIG. 5, showing its internal components.
Figure 6B:
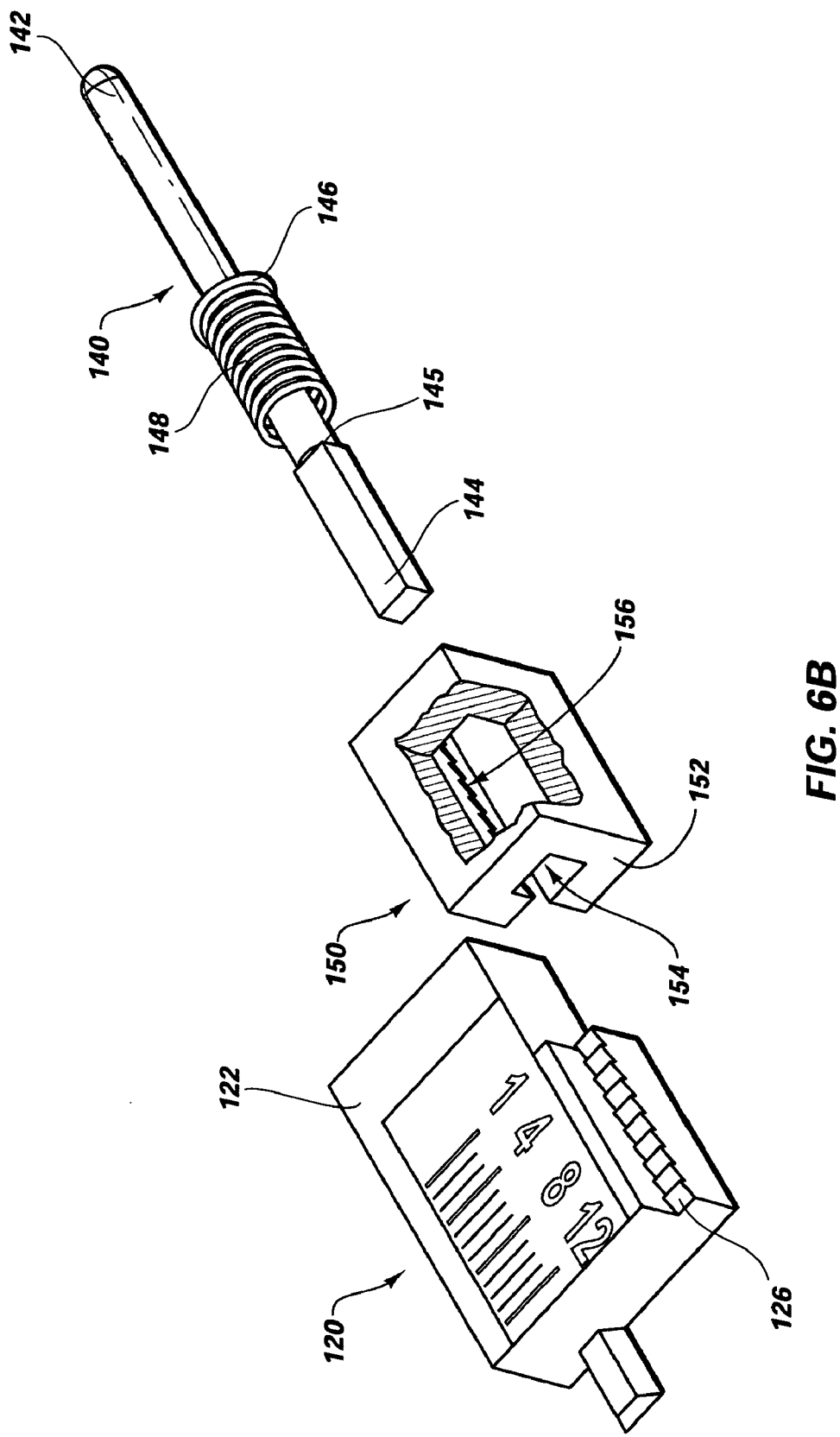
FIG. 6B is a partial cut-away perspective view of several of the internal components of the embodiment shown in FIG. 5.

FIGS. 6A and 6B are partial cross-sectional views of electrosurgical apparatus 100 illustrating the components of electrosurgical counter/lockout mechanism 110 and one manner in which temperature actuated element 170 and a mechanically actuated element (i.e. mechanical plunger 140) are linked to actuator 150 (see FIG. 6B). In the illustrated embodiment of FIG. 6A, temperature actuated element 170 is positioned in a seat 176 formed in housing 102 of electrosurgical apparatus 100. A distal end 174 of temperature actuated element 170 engages seat 176 to prevent movement of temperature actuated element 170 in the direction of power cord 104. A proximal end 172 of temperature actuated element 170 engages actuator 150 (not shown).

As the temperature of temperature actuated element 170 increases (e.g. during a sterilization procedure), the stiffness and strength of temperature actuated element 170 increases while the flexibility of temperature actuated element 170 decreases. Stiffening of temperature actuated element 170 reduces the degree of curvature of temperature actuated element 170. When temperature actuated element 170 is subjected to sufficient heat it changes from its substantially curved configuration to a more linear and rigid configuration in which proximal end 172 pushes actuator 150 in the direction of prongs 108*a–c*.

By utilizing a pushing motion, temperature actuated element 170 reduces the cost and complexity of manufacturing counter/lockout mechanism 110 while improving reliability of the system. This is due to the fact that stiffening of temperature actuated element 170 effectively moves actuator 150 without requiring precise engineering of the size, thickness, and length of temperature actuated element. This reduces the cost of designing and manufacturing temperature actuated element 170. Additionally, temperature actuated element 170 need not be integrally coupled to other components of electrosurgical counter/lockout mechanism 110 to maintain the tolerances that can be required in pull actuated devices. Instead, temperature actuated element 170 can be positioned in seat 176 substantially reducing the complexity, cost, and difficulty of assembling electrosurgical counter/lockout assembly 110.

In the illustrated embodiment, proximal end 142 of plunger 140 is positioned external to housing 102 of electrosurgical apparatus 100. Distal end 144 of mechanical plunger 140 is adapted to be positioned internal to actuator 150 (see FIG. 6B). Distal end 144 of mechanical plunger 140 engages actuator 150 to cause movement of actuator 150 when mechanical plunger 140 is depressed. An engagement ridge 145 (see FIG. 6B) of mechanical plunger 140 engages an engagement member 190 that is coupled to housing 102 of electrosurgical apparatus 100. Engagement member 190 prevents movement of engagement ridge 145 past a given position in the direction of prongs 108*a–c*. As a result, movement of proximal end 142 of mechanical plunger 140, in the direction of prongs 108*a–c*, is prevented past a given position.

A bias spring 148 circumscribes a portion of plunger 140 and such that it is positioned between a flange 146 of plunger 140 and engagement member 190. Bias spring 148 provides a biasing force in the direction of prongs 108*a–c* to push proximal end 142 of mechanical plunger 140 outside housing 102 when mechanical plunger 140 is not being depressed by contact with the wall outlet, socket, or other impediment. When mechanical plunger 140 is depressed, distal end 144 moves in the direction of power cord 104. Distal end 144 interacts with an internal surface of actuator 150 (see FIG. 6B) to move actuator 150 in the direction of power cord 104. As will be appreciated by those skilled in the art, a variety of types and configurations of mechanical plungers can be utilized without departing from the scope and spirit of the present invention. For example, in one embodiment, the mechanical plunger can remain in the depressed configuration absent an external depressive force.

FIG. 6B illustrates actuator 150 separate from several of the components of the counter/lockout mechanism for the sake of simplicity and to more clearly illustrate operation of the components of the counter/lockout mechanism. In the illustrated embodiment, actuator 150 includes a body 152, a channel 154, and teeth 156. Body 152 maintains the rigidity and structure of actuator 150 providing adequate strength to move indicator 122 when engaged by temperature actuated element 170 (see FIG. 6A) and mechanical plunger 140. Channel 154 is defined by body 152 and is adapted to accommodate distal end 144 of mechanical plunger 140. This maintains the orientation of actuator 150 while minimizing lateral movement of the distal end 144 of mechanical plunger 140. Teeth 156 are formed in body 152 of actuator 150. Teeth 156 of actuator 150 engage teeth 126 of indicator 122. When actuator 150 is moved in the rearward direction the configuration of teeth 156 and teeth 126 result in movement of indicator 122 in the rearward direction. When actuator 150 is moved in the forward direction the configuration of teeth 156 and teeth 126 does not cause movement of indicator 122.

Returning to FIG. 6A, indicator assembly 120 includes an indicator 122 and a guide 129. Indicator 122 is adapted to move relative to other components of electrosurgical apparatus 100 to indicate a change in the number of sterilization/use cycles that have been completed. Guide 129 cooperatively engages indicator 122 to minimize lateral movement of indicator 122 and to ensure smooth and efficient sliding of indicator 122 in response to movement by actuator 150. In the illustrated embodiment, guide 129 includes a raised slide that is positioned within a groove formed in the bottom of indicator 122.

As will be appreciated by those skilled in the art, a variety of types and configurations of guides can be utilized without departing from the scope and spirit of the present invention.

In one embodiment, the guide includes a plurality of teeth (not shown) that prevent inadvertent movement of the indicator. In another embodiment, a non-slip substance (not shown) is positioned between the top of guide and the bottom surface of the indicator to prevent inadvertent movement of the indicator. In another embodiment, the guide includes a surface that creates sufficient frictional contact with the indicator to prevent inadvertent movement of the indicator, i.e., any movement not caused by movement of the mechanical plunger against the actuator.

Teeth 126 are formed in indicator 122. Teeth 126 engage teeth 156 of actuator 150. In the illustrated embodiment, the configuration of teeth 126 and teeth 156 are such that when actuator 150 is moved in the direction of prongs 108*a–c*, actuator 150 is displaced relative to indicator 122 and no movement of indicator 122 occurs. When actuator 150 is moved in the direction of power cord 104, in response to depression of mechanical plunger 140, teeth 156 of actuator 150 engage teeth 126 of indicator assembly 120 and move indicator 122 in the direction of power cord 104.

In one embodiment, the force required to move the actuator in the direction of the prongs is substantially less than the amount of force required to move the actuator and the indicator in the direction of the power cord. In another embodiment, the amount of force provided by the temperature actuated element to move the actuator is substantially less than the amount of force the mechanically actuated element provides to move the actuator and the indicator. In the illustrated embodiment, the mechanical plunger 140 exerts a force on actuator 150. Actuator 150 then engages and relays the force necessary to move indicator 122. Movement of actuator 150 and indicator 122 in response to sterilization/use cycles will be discussed in greater detail with reference to FIGS. 7 and 8.

Indicator 122 further includes a lockout portion 128. Lockout portion 128 includes a void adapted to accommodate actuator 150 when indicator 122 has moved to a displacement closer to power cord 104. Movement of actuator 150 allows mechanical plunger 140 to move to its greatest proximal displacement relative to prongs 108*a–c* while the juxtaposition of lockout portion 128, actuator 150, and distal end 144 of plunger 140 prevents movement of distal end 144 of mechanical plunger 140 toward power cord 104.

Figure 7:
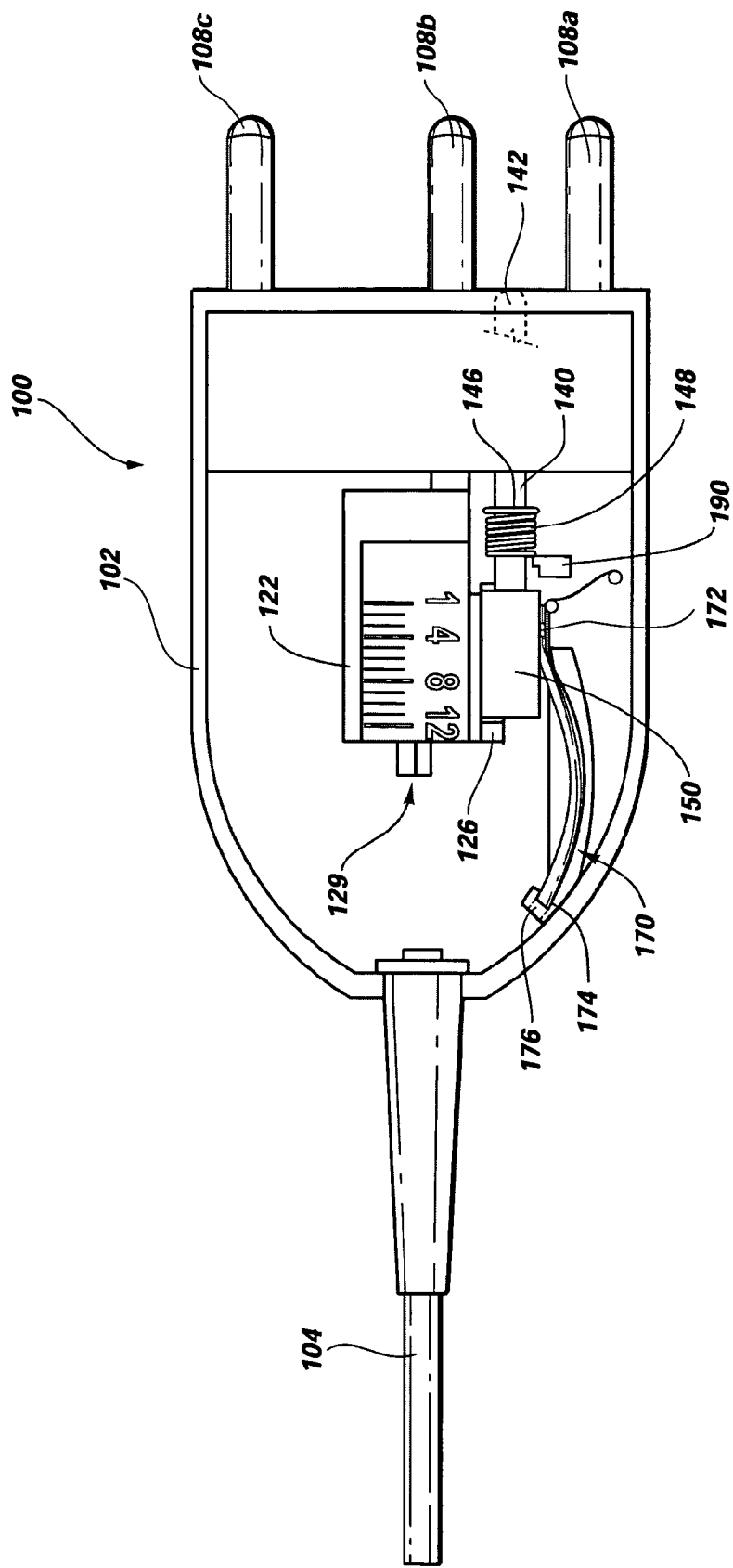
FIG. 7 is a top internal view of the embodiment shown in FIG. 5, illustrating the mechanical plunger in a fully depressed position.

FIG. 7 illustrates an internal view of electrosurgical apparatus 100 illustrating movement of indicator 122 in response to movement of mechanical plunger 140, when comparing the positions of indicator 122 in FIG. 5 and FIG. 7. In FIG. 7, mechanical plunger 140 is depressed such that the entire length of mechanical plunger 140 is positioned internal to housing 102. As previously discussed, distal end 144 (see FIG. 6B) of mechanical plunger 140 engages actuator 150. This causes movement of actuator 150 in the direction of power cord 104. As actuator 150 moves in the direction of power cord 104, teeth 156 of actuator 150 engage teeth 126 (FIG. 6B) of indicator 122. This causes movement of indicator 122 in the direction of power cord 104. When indicator 122 moves in the direction of power cord 104 a change of indicia is effectuated showing to the user the number of remaining uses subsequent to a completed sterilization/use cycle. Additionally, as actuator 150 is moved in the direction of power cord 104, temperature actuated element 170 is returned to a configuration having a greater degree of curvature under the influence or force applied to actuator 150 by mechanical plunger 140. The greater degree of curvature of temperature actuated element 170 results when temperature actuated element 170 is not subject to the temperatures that result in the increased rigidity of temperature actuated element 170. As a result, temperature actuated element 170 provides minimal resistance allowing proximal end 172 to be moved closer to distal end 174 engaged in seat 176.

As mechanical plunger 140 is depressed, flange 146 is moved closer to engagement member 190 causing additional compression of bias spring 148. The compression of bias spring 148 exerts a force on flange 146 such that proximal end 142 will extend from housing 102 of electrosurgical apparatus 100 once a counteracting force is no longer exerted on the proximal end of mechanical plunger 140. Once actuator 150 is positioned in the present position, unplugging and subsequent insertion of prongs 108a–c into an outlet will not result in additional movement of actuator 150. This is due to the fact that the distal end of plunger 140 is slidably engaged within actuator 150. Movement of mechanical plunger 140 in the direction of prongs 108a–c does not result in movement of actuator 150 in the direction of prongs 108a–c. As a result, a user may plug and unplug prongs 108a–c multiple times without decrementing indicator 122.

FIG. 8 illustrates electrosurgical counter/lockout mechanism 110 during a sterilization cycle. In the illustrated embodiment, temperature actuated element 170 has moved from the curved configuration illustrated in FIG. 7 to a more linear configuration. The more linear configuration is a result of the increased rigidity resulting from temperature changes experienced during a sterilization cycle. The increased rigidity provides a tensile strength that exceeds the tensile strength experienced when temperature actuated element 170 is not subjected to high temperatures. In its more linear configuration, proximal end 172 of temperature actuated element 170 pushes actuator 150 in the direction of prongs 108a–c.

Due to the configuration of teeth 126 of indicator 122 and the teeth of actuator 150, movement of actuator 150 in the direction of prongs 108a–c does not result in movement of indicator 122. Additionally, repeated heating and cooling of temperature actuated element 170 will not result in multiple increments and/or decrements of the counter as movement of indicator 122 occurs only in response to depression of mechanical plunger 140. As a result, actuator 150 does not effectuate a change of the indicia until both temperature actuated element 170 has experienced a sterilization cycle moving actuator 150 in one direction and mechanical plunger 140 has experienced a use cycle moving actuator 150 in the opposite direction.

As a number of sterilization/use cycles are being conducted, indicator 122 will continue to move further and further in the direction of power cord 104. As indicator 122 moves further in the direction of power cord 104 different indicia are displayed indicating to the user changes in the number of remaining uses left with respect to electrosurgical apparatus 100. As will be appreciated by those skilled in the art, a variety of types and configurations of electrosurgical counter/lockout mechanisms 110 can be utilized without departing from the scope and spirit of the present invention. For example in one embodiment, the temperature actuated element moves the actuator and the indicator while the mechanical plunger displaces the actuator relative to the indicator. In another embodiment, one or both of the temperature actuated element and the plunger are not directly connected to the actuator but move the actuator indirectly. In another embodiment, the temperature actuated element and the plunger cause a change of indicia without the use of an actuator. In another embodiment, the actuator pulls the indicator to cause movement of the indicator.

FIG. 9 illustrates electrosurgical counter/lockout mechanism 110 in which indicator 122 has been moved to a displacement nearest to power cord 104 and mechanical plunger 140 is in a lockout position. Once indicator 122 is moved to its displacement closest to power cord 104, lockout portion 128 is positioned adjacent actuator 150. A leaf spring 180 exerts a lateral force on actuator 150 in the direction of indicator 122. The positioning of indicator 122 at the displacement closest to power cord 104 allows lockout portion 128 to accommodate actuator 150. This results in lateral displacement of actuator 150 into lockout portion 128 of indicator 122.

Distal end 144 of mechanical plunger 140 is positioned in channel 154 (see FIG. 6B) of actuator 150. Lateral movement of the actuator 150 into lockout portion 128 results in lateral movement of distal end 144 of mechanical plunger 140 in the direction of indicator 122. Lateral movement of distal end 144 results in disengagement of engagement ridge 145 from engagement member 190 (see FIG. 6B). As a result, engagement member 190 can no longer counteract the force exerted by bias spring 148 on flange 146, and thus mechanical plunger 140, in the direction of prongs 108a–c. In the illustrated embodiment, bias spring 148 exerts a force onto flange 146 in the direction of prongs 108a–c extending proximal end 142 of mechanical plunger 140 from housing 102 approximately the same length of prongs 108a–c. In another embodiment, the mechanical plunger extends from the housing a length that does not approximate the length of the prongs.

When electrosurgical apparatus 100 has completed its final sterilization/use cycle, indicator 122 is positioned in contact with stop 125. Stop 125 is formed from the lower portion of housing 102. Additional movement of indicator 122 in the direction of power cord 104 is prevented by stop 125. Movement of actuator 150 in the direction of the power cord 104 is prevented by lockout portion 128 when actuator 150 is pushed into engagement with lockout portion 128. Movement of mechanical plunger in the direction of power cord 104 is prevented by contact between distal end 144 of mechanical plunger 140 and the front surface of actuator 150.

When actuator 150 is pushed into engagement with lockout portion 128 lateral displacement of actuator 150 occurs. The lateral displacement of actuator 150 positions channel 154 out of alignment with distal end 144 of mechanical plunger 140. As a result, distal end 144 of mechanical plunger 140 contacts the front surface of actuator 150 instead of sliding into channel 154. Additionally, leaf spring 180 engages actuator 150 preventing lateral movement of actuator and ensuring that distal end 144 of mechanical plunger 140 does not slide back into channel 154 of actuator 150.

The contact between front surface of actuator 150 and distal end 144 of mechanical plunger 140 prevents movement of mechanical plunger 140 in direction of power cord 104. In other words, the juxtaposition of indicator 122, actuator 150, and mechanical plunger 140 prevents mechanical plunger 140 from being pushed into housing 102. As a result, once the predetermined number of sterilization/use cycles have been completed, mechanical plunger 140 prevents use of electrosurgical apparatus 100 when a user attempts to insert prongs 108a–c into an electrosurgical power source (not shown).

As will be appreciated by those skilled in the art, a variety of types and configurations of lockout mechanisms can be utilized without departing from the scope and spirit of the present invention. For example, in one embodiment, the lockout mechanism disconnects an internal electrical connection preventing the flow of electrosurgical current in the electrosurgical apparatus. In another embodiment, the lockout mechanism prevents coupling of portions of a modular electrosurgical apparatus effectively preventing use of the electrosurgical apparatus.

With reference now to FIG. 10, there is shown an alternative configuration of an electrosurgical counter/lockout mechanism according to one aspect of the present invention. In the illustrated embodiment, a temperature actuated element 270 and a mechanically actuated element (i.e. mechanical plunger 240) engage an actuator 250. Actuator 250 causes movement of an indicator 222. In the illustrated embodiment, indicator 222 is a rotary type indicator having a plurality of teeth 226 and a plurality of indicia 224. Teeth 226 are engaged by actuator 250 to rotate indicator 222. Movement of indicator 222 results in display of a different one of the plurality of indicia 224 positioned on indicator 222.

Much like the electrosurgical counter/lockout mechanism of FIGS. 1–9, plunger 240 of counter/lockout mechanism 210 is moved into the housing during a use cycle. This causes rotation of indicator 222 due to engagement of teeth formed in actuator 250 (not shown) mating with one or more teeth 226 of indicator 222. Temperature actuated element 270 is actuated in response to the heat used in a sterilization cycle. Temperature actuated element 270 stiffens in response to a sterilization cycle causing movement of actuator 250 in the direction of the prongs of the electrosurgical apparatus. This positions actuator 250 such that depression of the mechanical plunger 240 in response to a use cycle will cause rotation of indicator 222. The configuration of the temperature actuated element 270 and mechanical plunger 240 ensure that a single change of the positioning of indicia 224 on indicator 222 is effectuated for each sterilization/use cycle.

In the illustrated embodiment, indicator 222 includes a lockout portion 228. Lockout portion 228 is configured to accommodate a proximal portion of plunger 240 and/or a portion of actuator 250 to prevent plunger 240 from being forced into the housing of the electrosurgical apparatus once a predetermined number of sterilization/use cycles have been completed. In the illustrated embodiment, once the predetermined number of sterilization/use cycles have been completed, lockout portion 228 is positioned adjacent actuator 250. Lateral biasing member 280 exerts a lateral biasing force on mechanical plunger 240 causing movement of the proximal portion of mechanical plunger 240 in the direction of indicator 222. Lateral movement of mechanical plunger 240 results in disengagement of mechanical plunger 240 from engagement member 290 allowing bias spring 248 to move mechanical plunger 240 such that the distal end of mechanical plunger 240 is extended approximately the same length as the adjacent prongs. Once mechanical plunger 240 is extended, the lateral movement of mechanical plunger 240 and lateral biasing member 280 moves mechanical actuator 250 into engagement with lockout portion 228 to prevent the proximal portion of mechanical plunger 240 from being repositioned inside actuator 250. As a result, retraction of mechanical plunger 240 inside the housing of the electrosurgical apparatus is prevented.

As will be appreciated by those skilled in the art, a variety of types and configurations of indicators can be utilized without departing from the scope and spirit of the present invention. For example, in one embodiment the indicator includes a plurality of indicia that are movable separate from movement of the indicator. According to another embodiment of the present invention, the indicator comprises a seven segment display that increments based on an analog or digital signal.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A counter to track the number of sterilization/use cycles an electrosurgical apparatus has undergone, the counter comprising:
    a means for detecting a temperature above ambient associated with a sterilization cycle, the means for detecting a temperature above ambient comprising a temperature actuated member, the temperature actuated member comprising a shape memory;
    means for detecting a use cycle of the apparatus, the means for detecting a temperature above ambient and the means for detecting a use cycle combining to effectuate a change of one or a plurality of indicia to show that a single sterilization/use cycle has been completed for each sterilization/use cycle undergone.

2. The electrosurgical counter of claim 1, further comprising an indicator having a plurality of indicia for illustrating changes in the number of sterilization/use cycles completed.

3. The electrosurgical counter of claim 1, further comprising an actuator.

4. The electrosurgical counter of claim 3, wherein the actuator is linked to the indicator, means for detecting a temperature above ambient, and the means for detecting a use cycle.

5. The electrosurgical counter of claim 4, wherein the actuator causes a change in the one or plurality of indicia to illustrate to the user changes in the number of sterilization/use cycles undergone or remaining.

6. The electrosurgical counter of claim 5, wherein the actuator moves in a first direction when the means for detecting a temperature above ambient is actuated.

7. The electrosurgical counter of claim 6, wherein the actuator moves in a second direction when the means for detecting a use cycle is actuated.

8. The electrosurgical counter of claim 7, wherein the actuator moves the indicator such that the indicator shows that a single sterilization/use cycle has been completed subsequent to moving in the first direction and the second direction subsequent to a completed sterilization/use cycle.

9. An electrosurgical counter to track the number of sterilization/use cycles an electrosurgical apparatus has undergone, the electrosurgical counter comprising:
    an indicator having a plurality of indicia for illustrating changes in the number of sterilization/use cycles completed;
    a temperature actuated element linked to the indicator;
    a mechanically actuated element linked to the indicator, the mechanically actuated element comprising a plunger and being actuated during a sterilization cycle such that the plunger is biased into the electrosurgical apparatus during a use cycle, the temperature actuated element and the mechanically actuated element effectuating a change of the indicia such that the indicator shows that a single sterilization/use cycle has been completed for each sterilization/use cycle undergone.

10. The electrosurgical counter of claim 9, wherein the temperature actuated element is actuated during a sterilization cycle.

11. The electrosurgical counter of claim 9, wherein the plunger is depressed and is biased into the electrosurgical apparatus when the electrosurgical apparatus is plugged into an electrosurgical power source.

12. The electrosurgical counter of claim 9, wherein the indicator illustrates the number of remaining uses for the electrosurgical apparatus.

13. The electrosurgical counter of claim 9, wherein the indicator illustrates the number of sterilization/use cycles the electrosurgical apparatus has undergone.

14. An electrosurgical counter to track the number of sterilization/use cycles an electrosurgical apparatus has undergone, the electrosurgical counter comprising:
an indicator having one or a plurality of indicia for illustrating changes in the number of sterilization/use cycles completed;
a temperature actuated element linked to the indicator; and
a mechanically actuated element linked to the indicator, the temperature actuated element and the mechanically actuated element effectuating a change of the one or plurality of indicia such that the indicator shows that a single sterilization/use cycle has been completed for each sterilization/use cycle undergone, wherein the one or plurality of indicia move relative to the indicator.

15. An electrosurgical counter to track the number of sterilization/use cycles an electrosurgical apparatus has undergone, the electrosurgical counter comprising:
an indicator having one or a plurality of indicia for illustrating changes in the number of sterilization/use cycles completed;
a temperature actuated element linked to the indicator;
a mechanically actuated element linked to the indicator, the temperature actuated element and the mechanically actuated element effectuating a change of the one or plurality of indicia such that the indicator shows that a single sterilization/use cycle has been completed for each sterilization/use cycle undergone wherein the one or plurality of indicia does not move relative to the indicator and wherein the indicator moves to illustrate a different one of the indicia to the user.

16. An electrosurgical sterilization/use counter, comprising:
an indicator having a plurality of indicia for illustrating the number of remaining uses before the electrosurgical apparatus should be discarded;
an actuator linked to the indicator;
a temperature actuated element linked to the actuator and being actuated in response to a sterilization cycle, the temperature actuated element moving the actuator in a first direction when actuated, the temperature actuated element pushes the actuator to move the actuator in the first direction wherein the temperature actuated element comprises a shape memory alloy; and
a mechanically actuated element linked to the actuator, the mechanically actuated element moving the actuator in a second direction, the temperature actuated element and the mechanically actuated element causing the actuator to effect a change of indicia to show the number of remaining uses subsequent to a sterilization/use cycle.

17. The electrosurgical sterilization/use counter of claim 16, wherein the shape memory alloy is in a curved configuration during use of the electrosurgical apparatus.

18. The electrosurgical sterilization/use counter of claim 17, wherein the shape memory alloy is in a stiffened substantially linear configuration during at least a portion of a sterilization cycle.

19. The electrosurgical sterilization/use counter of claim 18, wherein the shape memory alloy pushes the actuator to cause movement of the indicator.

20. An electrosurgical lockout mechanism for use with an electrosurgical apparatus configured to be discarded after a predetermined number of sterilization/use cycles, the electrosurgical lockout mechanism comprising:
an indicator having a plurality of indicia for showing the number of remaining uses before the electrosurgical apparatus should be discarded;
an actuator configured to engage the indicator to illustrate a different one of the indicia to show the number of remaining uses;
a temperature actuated element linked to the actuator, the temperature actuated element being adapted to move the actuator in a first direction;
a mechanically actuated element linked to the actuator, the mechanically actuated element adapted to move the actuator in a second direction; and
a lockout mechanism linked to the actuator the lockout mechanism comprising a mechanical plunger, the lockout mechanism adapted to be utilized with the temperature actuated element and the mechanically actuated element, wherein the lockout mechanism is also adapted to prevent use of the electrosurgical apparatus when the electrosurgical apparatus has undergone a predetermined number of sterilization/use cycles.

21. The electrosurgical lockout mechanism of claim 20, wherein the mechanical plunger comprises the mechanically actuated element.

22. The electrosurgical lockout mechanism of claim 21, wherein the mechanical plunger prevents a user from connecting the electrosurgical apparatus to an electrosurgical power source.

23. The electrosurgical lockout mechanism of claim 20, wherein the lockout mechanism is utilized with a modular electrosurgical apparatus.

24. An electrosurgical lockout mechanism for use with an electrosurgical apparatus configured to be discarded after a predetermined number of sterilization/use cycles, the electrosurgical lockout mechanism comprising:
an indicator having a plurality of indicia for showing the number of remaining uses before the electrosurgical apparatus should be discarded;
an actuator configured to engage the indicator to illustrate a different one of the indicia to show the number of remaining uses;
a temperature actuated element linked to the actuator, the temperature actuated element being adapted to move the actuator in a first direction;
a mechanically actuated element linked to the actuator, the mechanically actuated element adapted to move the actuator in a second direction; and
a lockout mechanism linked to the actuator, the lockout mechanism adapted to be utilized with the temperature actuated element and the mechanically actuated element, wherein the lockout mechanism is also adapted to prevent use of the electrosurgical apparatus when the electrosurgical apparatus has undergone a predetermined number of sterilization/use cycles, the lockout mechanism being utilized with a modular electrosurgical apparatus wherein the lockout mechanism prevents use of the modular electrosurgical apparatus by preventing coupling of different portions of the modular electrosurgical apparatus.

25. An electrosurgical sterilization/use counter for use with a reusable electrosurgical apparatus being configured to accurately show the number of remaining uses subsequent to a sterilization/use cycle, the electrosurgical sterilization/use counter comprising:
an indicator having a plurality of indicia for illustrating to the user the number of remaining uses before the electrosurgical apparatus should be discarded;
an actuator linked to the indicator;
a temperature actuated element linked to the actuator; and
a mechanically actuated element linked to the actuator, wherein one of the temperature actuated element or the mechanically actuated element moves the actuator in a first direction to effect a change of indicia, and wherein the actuator is prevented from effecting a subsequent change of the indicia until the other one of the temperature actuated element or the mechanically actuated element moves the actuator in a second direction.

26. The electrosurgical sterilization/use counter of claim 25, wherein the indicator is in a linear configuration.

27. The electrosurgical sterilization/use counter of claim 26, wherein the indicator is slidable in a linear direction.

28. The electrosurgical sterilization/use counter of claim 25, wherein the indicator has a circular configuration.

29. The electrosurgical sterilization/use counter of claim 25, wherein the indicator is rotatable to display a different one of the indicia.

30. The electrosurgical sterilization/use counter of claim 25, wherein the indicator comprises a display.

31. The electrosurgical sterilization/use counter of claim 30, wherein the display comprises a seven segment display.

32. The electrosurgical sterilization/use counter of claim 31, wherein the display comprises one of a digital display, a mechanical display, or an electronic display.

33. The electrosurgical sterilization/use counter of claim 25 further comprising a mechanism for minimizing inadvertent movement of the indicator.

* * * * *

UNITED STATES PATENT AND TRADEMARK OFFICE
CERTIFICATE OF CORRECTION

PATENT NO.       : 7,124,932 B2                                    Page 1 of 1
APPLICATION NO.  : 10/873380
DATED            : October 24, 2006
INVENTOR(S)      : Isaacson et al.

It is certified that error appears in the above-identified patent and that said Letters Patent is hereby corrected as shown below:

Column 4
Line 21, change "direction the" to --direction, the--

Column 6
Line 34, after "etc.)", insert --.--

Column 11
Line 32, change "direction but" to --direction, but--

Column 22
Line 21, change "FIG. 6B" to --FIG. 6A--

Signed and Sealed this

Seventeenth Day of June, 2008

JON W. DUDAS
*Director of the United States Patent and Trademark Office*